(12) United States Patent
Bartfeld et al.

(10) Patent No.: US 9,295,416 B2
(45) Date of Patent: Mar. 29, 2016

(54) CAPILLARY ACTION COLLECTION DEVICE AND CONTAINER ASSEMBLY

(75) Inventors: Benjamin Bartfeld, Pompton Lakes, NJ (US); Bradley M. Wilkinson, North Haledon, NJ (US); Ajit Dastane, Bridgewater, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 830 days.

(21) Appl. No.: 12/398,777

(22) Filed: Mar. 5, 2009

(65) Prior Publication Data

US 2009/0259145 A1 Oct. 15, 2009

Related U.S. Application Data

(60) Provisional application No. 61/034,025, filed on Mar. 5, 2008.

(51) Int. Cl.
| | | |
|---|---|---|
| *A61B 5/15* | (2006.01) | |
| *A61B 10/00* | (2006.01) | |
| *B01L 3/00* | (2006.01) | |
| *A61B 5/154* | (2006.01) | |

(52) U.S. Cl.
CPC ............. *A61B 5/1405* (2013.01); *A61B 5/1438* (2013.01); *A61B 5/154* (2013.01); *A61B 5/150022* (2013.01); *A61B 5/150259* (2013.01); *A61B 5/150267* (2013.01); *A61B 5/150343* (2013.01); *A61B 5/150351* (2013.01); *A61B 10/0096* (2013.01); *B01L 3/5021* (2013.01); *B01L 2200/026* (2013.01); *B01L 2300/042* (2013.01); *B01L 2300/047* (2013.01); *B01L 2300/0609* (2013.01); *B01L 2300/0672* (2013.01); *B01L 2300/087* (2013.01); *B01L 2300/0838* (2013.01); *B01L 2400/0409* (2013.01)

(58) Field of Classification Search
USPC ......... 220/23.87, 23.88, 23.89; 600/573, 575, 600/576; 422/549
See application file for complete search history.

(56) References Cited

U.S. PATENT DOCUMENTS 3,630,191 A * 12/1971 Gilford .......................... 600/575
4,024,857 A * 5/1977 Blecher et al. ................ 600/576
4,156,570 A 5/1979 Wardlaw (Continued)

FOREIGN PATENT DOCUMENTS

| CN | 1183260 A | 6/1998 |
|---|---|---|
| DE | 1187954 B | 2/1965 |

(Continued)

*Primary Examiner* — Sean Dougherty
(74) *Attorney, Agent, or Firm* — The Webb Law Firm

(57) ABSTRACT

A container assembly is disclosed including an outer container, a hollow inner member, and a closure. The outer container has a closed bottom, an open top, and a sidewall extending therebetween. The hollow inner member is disposed within the outer container and has an inner surface defining at least one capillary channel. The inner member includes a first end adjacent to the open top of the outer container and has an outer periphery seated against the sidewall of the outer container. The closure has a proximal end and a distal end. The closure proximal end is seated at least partially within the first end of the inner member to seal the outer container and inner member and define a fluid collection chamber. The closure distal end defines a recessed area shaped to direct fluid under capillary action to the at least one capillary channel in the inner member.

12 Claims, 21 Drawing Sheets

(56) References Cited

U.S. PATENT DOCUMENTS

| | | | |
|---|---|---|---|
| 4,558,947 A | 12/1985 | Wardlaw | |
| 4,620,549 A * | 11/1986 | Nugent | 600/576 |
| 4,818,386 A | 4/1989 | Burns | |
| 4,967,919 A | 11/1990 | Earhart | |
| 5,038,794 A | 8/1991 | Van Valkenburg | |
| 5,215,102 A | 6/1993 | Guirguis | |
| 5,384,096 A * | 1/1995 | Burns | 422/549 |
| 5,458,854 A * | 10/1995 | Burns | 422/549 |
| 5,632,895 A | 5/1997 | Tsukagoshi et al. | |
| 5,634,474 A | 6/1997 | Grippi | |
| 5,779,074 A | 7/1998 | Burns | |
| 5,788,863 A * | 8/1998 | Milunic | 210/651 |
| 5,888,184 A | 3/1999 | Wardlaw | |
| 5,889,581 A | 3/1999 | Tokuda | |
| 5,889,584 A | 3/1999 | Wardlaw | |
| 6,077,235 A | 6/2000 | Serpentino et al. | |
| 6,080,366 A | 6/2000 | Kelly et al. | |
| 6,155,991 A * | 12/2000 | Beat et al. | 600/573 |
| 6,171,261 B1 * | 1/2001 | Niermann et al. | 600/573 |
| 6,551,267 B1 | 4/2003 | Cohen et al. | |
| 6,651,835 B2 | 11/2003 | Iskra | |
| 6,793,892 B1 | 9/2004 | Niermann | |
| 6,910,597 B2 | 6/2005 | Iskra | |
| 7,097,057 B2 | 8/2006 | Classens | |
| 2002/0094305 A1 | 7/2002 | Dicesare et al. | |
| 2002/0131904 A1 | 9/2002 | DiCesare et al. | |
| 2004/0050846 A1 | 3/2004 | Iskra | |
| 2004/0176704 A1 * | 9/2004 | Stevens et al. | 600/584 |
| 2005/0196872 A1 | 9/2005 | Nguyen et al. | |
| 2007/0168051 A1 * | 7/2007 | Bronnenberg | H04N 21/4332 700/20 |
| 2007/0168851 A1 * | 7/2007 | Hunt | H05B 37/029 715/209 |
| 2007/0168852 A1 * | 7/2007 | Erol | G06F 17/30044 715/234 |
| 2007/0168862 A1 * | 7/2007 | Hunt | H05B 37/029 715/705 |
| 2007/0174758 A1 * | 7/2007 | Ando | G11B 20/00086 715/203 |
| 2007/0174917 A1 * | 7/2007 | Guruswamy | H04L 63/1433 726/25 |

FOREIGN PATENT DOCUMENTS

| | | |
|---|---|---|
| EP | 0224650 A2 | 6/1987 |
| EP | 0311011 A2 | 4/1989 |
| EP | 0638804 A1 | 2/1995 |
| EP | 0740155 A1 | 10/1996 |
| JP | 62-133936 A | 6/1987 |
| JP | 06-504130 A | 5/1994 |
| JP | 08-299309 A | 11/1996 |
| JP | 2000-189407 A | 7/2000 |
| JP | 2002-148152 A | 5/2002 |

* cited by examiner

CAPILLARY ACTION COLLECTION DEVICE AND CONTAINER ASSEMBLY

CROSS REFERENCE TO RELATED APPLICATION

This application claims priority to U.S. Provisional Patent Application No. 61/034,025, filed Mar. 5, 2008, entitled "Capillary Action Collection Device and Container Assembly", the entire disclosure of which is herein incorporated by reference.

BACKGROUND OF THE INVENTION

1. Field of the Invention

The present invention relates to a device for the collection, storage, and transfer of a blood or specimen sample obtained from a patient for medical diagnostic testing. More specifically, the present invention relates to a device for collection of blood samples from a patient. The device also includes a cap assembly having a stopper for closing and sealing the device after the blood or specimen sample has been collected. The stopper incorporates space elimination features to funnel the blood or specimen sample to a probe assembly of a testing instrument during transfer from the collection tube.

2. Description of Related Art

Conventional capillary collection devices typically provide a microtube or collection container having a raised receiving lip or funnel feature that engages the skin surface of a patient that has been pierced, so as to draw a blood sample from the capillaries located just beneath the skin surface. The internal collection cavities of conventional collection containers are typically straight-walled and do not provide any specimen flow-enhancing features. Conventional containers typically do not promote the flow of drawn blood into the cavity during the collection process, and a typically not structured to allow direct withdrawal of a sample from within the cavity by standard instrumentation. Accordingly, a significant amount of the collected blood or specimen sample is trapped on the sidewall of the cavity due to surface tension during collection and during transfer.

After collection, conventional collection containers are typically sealed by a cap assembly disposed on the collection container. Conventional cap assemblies typically provide a flat bottom surface in communication with the collection cavity. As a result, a significant dead volume amount of sample is trapped within the collection cavity during transfer of the specimen, since neither the collection container nor the cap assembly adequately funnel or channel the collected blood sample to the aspiration hole of the probe needle. As can be appreciated, conventional collection assemblies retain a significant amount of wasted sample within the container. This requires that a significantly greater volume of sample must be collected within the collection container than is actually required to perform the necessary diagnostic test. The volume of sample collected is particularly important in capillary applications, in which a very small volume of blood is typically available. The avoidance of waste specimen is therefore a particularly important concern. Also of concern is the exposure of a specimen to medical practitioners during the sampling procedure, and compatibility of the collection container with standard diagnostic and analysis instrumentation.

Accordingly, there is a need for a fluid sample collection device, container assembly, and associated fluid sample collection methods in which the amount of sample collection, typically blood collection, characteristics are improved. There is also a need for an improved collection assembly which is compatible with standard diagnostic and analysis instrumentation. There is further a need for an improved collection assembly in which exposure of medical practitioners to a specimen during a sampling process is reduced.

SUMMARY OF THE INVENTION

In one embodiment, a container assembly is disclosed including an outer container, a hollow inner member, and a closure. The outer container has a closed bottom, an open top, and a sidewall extending therebetween. The hollow inner member is disposed within the outer container and has an inner surface defining at least one capillary channel. The inner member includes a first end adjacent to the open top of the outer container and has an outer periphery seated against the sidewall of the outer container. The closure has a proximal end and a distal end. The closure proximal end is seated at least partially within the first end of the inner member to seal the inner member and the outer container and define a fluid sample chamber. The closure distal end defines a recessed area shaped to direct fluid under capillary action to the at least one capillary channel in the inner member.

The hollow member may extend from the open top to the closed bottom of the outer container and includes a second end supported against the closed bottom. The at least one capillary channel may extend longitudinally along the inner surface of the inner member. The at least one capillary channel may extend only a portion of the length of the inner surface of the inner member. The at least one capillary channel may include a plurality of capillary channels equally distributed around the inner surface of the inner member. The recessed portion of the closure may be concave or conically-shaped and may define at least one capillary channel therein.

The first end of the inner member may define a socket portion for receiving the closure proximal end, and the closure proximal end may include a collar portion for sealing against the socket portion. The socket portion may have retaining tabs for retaining the collar portion therein. The peripheral collar portion may include at least two sealing shoulders contacting the socket portion. The at least two sealing shoulders contact the socket at orthogonal locations.

The closure may have a closure body tapering inward from the closure proximal end to the closure distal end to define an annular space or cavity about the closure body with the inner surface of the inner member. A cap member may be in interlocking engagement with the closure.

Another aspect disclosed herein is a collector for accessing a container assembly. The collector includes a collector body having a proximal end and a distal end. A penetrating needle cannula may be associated with the distal end of the collector body, which is shaped to pierce an elastomeric closure on a sample collection container. Channel members may be provided on the collector body, which define intervening capillary channels to guide fluid to the penetrating needle cannula.

The rim portion may define a concave-shaped collection area. The collector body may define a central bore and at least one internal capillary channel may be defined in the central body in the bore for guiding fluid under capillary action to the penetrating needle cannula. The channel members may bulge upward from the rim portion. The penetrating needle cannula may define at least one longitudinally-extending capillary channel. Additionally, the penetrating needle cannula may define at least one longitudinally-extending capillary channel and at least one longitudinally-extending vent channel. The penetrating needle cannula may comprise a generally H-shaped transverse cross-sectional shape. Fingertabs extend outward from the collector body.

In another embodiment, a container assembly comprises an outer container, an inner member, a closure, and a wall element. The outer container comprises a closed bottom, an open top, and a sidewall extending therebetween. The hollow inner member is disposed within the outer container and has an inner surface. The inner member comprises a first end adjacent to the open top of the outer container and having an outer periphery seated against the sidewall of the outer container and a second end. The closure is seated at least partially within the first end of the inner member to seal the outer container and define a fluid collection chamber. The wall element adapted to seal against the inner surface of the inner member and adapted to move within the inner member under centrifugal force applied to the container assembly.

The inner member may define an internal rim at a transition location between a first internal diameter and a second internal diameter and the wall element may be seated in engagement with the internal rim such that, upon application of centrifugal force, the wall element compresses radially inward sufficiently to unseat from the internal rim and move downward in the inner member. The wall element may comprise a generally cylindrical body with at least one external flange engaged with the internal rim. The wall element may comprise a generally cylindrical body having a sidewall defining at least one capillary channel therein. The wall element body may comprise an upper portion and a lower portion, with the upper portion having a larger diameter than the lower portion. The generally cylindrical body may comprise a plurality of external flanges engaged with the internal rim. In use, upon application of centrifugal force to the container assembly, the plurality of external flanges desirably flex radially inward sufficiently such that the plurality of external flanges disengage from the internal rim and the wall element moves downward in the inner member.

In a further aspect, the inner member may define an internal rim at a transition location between a first internal diameter and a second internal diameter and the wall element may comprise a plurality of external flanges engaged with the internal rim. Upon application of centrifugal force to the container assembly, the plurality of external flanges may flex radially inward sufficiently to disengage from the internal rim In yet another embodiment, a container assembly includes a collection container having a closed bottom, an open top, and a sidewall extending therebetween having an inner surface defining at least one capillary channel. The container assembly also includes a closure having a proximal end and a distal end. The closure proximal end may be seatable at least partially within the open top of the collection container to seal the collection container and define a fluid sample chamber. The closure distal end may define a recessed area shaped to direct fluid under capillary action to the at least one capillary channel in the collection container.

In a further embodiment, a container assembly includes a collection container having a closed bottom, an open top, and a sidewall extending therebetween defining an interior. The collection container also includes a closure seatable at least partially within the open top of the collection container. A wall element may be disposed within the interior of the collection container, the wall element adapted to compress radially inward under centrifugal force applied to the container assembly to move downward within the interior.

In yet a further embodiment, a container assembly includes a collection container having a bottom, an open top, and a sidewall extending therebetween defining an interior. The container assembly also includes a closure seatable at least partially within the open top of the collection container. The container assembly further includes a wall element disposed within the interior of the collection container and movable from a first position to a second position under the application of a centrifugal force applied to the wall element in a direction away from the open top end towards the bottom.

In one configuration, the wall element has an element height, and travels less distance than the element height when moving from the first position to the second position. The wall element may be frictionally engaged with the collection container in both the first position and the second position, such that a frictional force exists between the wall element and the collection container. The frictional force may be greater in the second position than in the first position. Optionally, the wall element includes a tapered rim. The tapered rim may provide a sealing engagement between the wall element and the collection container in both the first position and the second position.

Further details and advantages will become clear upon reading the following detailed description in conjunction with the accompanying drawing figures, wherein like parts are designated with like reference numerals throughout.

DESCRIPTION OF PREFERRED EMBODIMENTS

Figure 1:
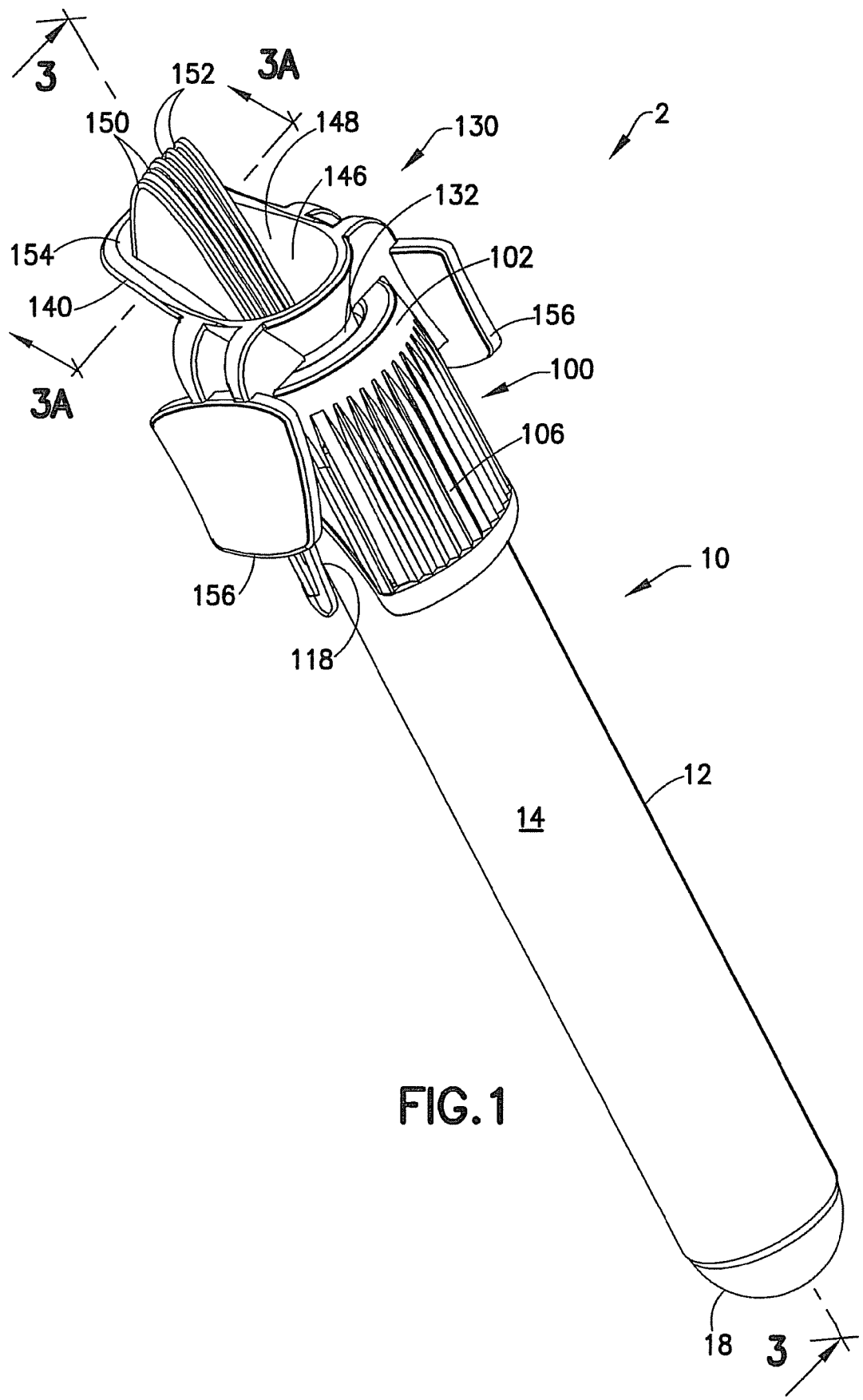
FIG. 1 is a perspective view of a fluid sample collection device pursuant to one embodiment.
Figure 2:
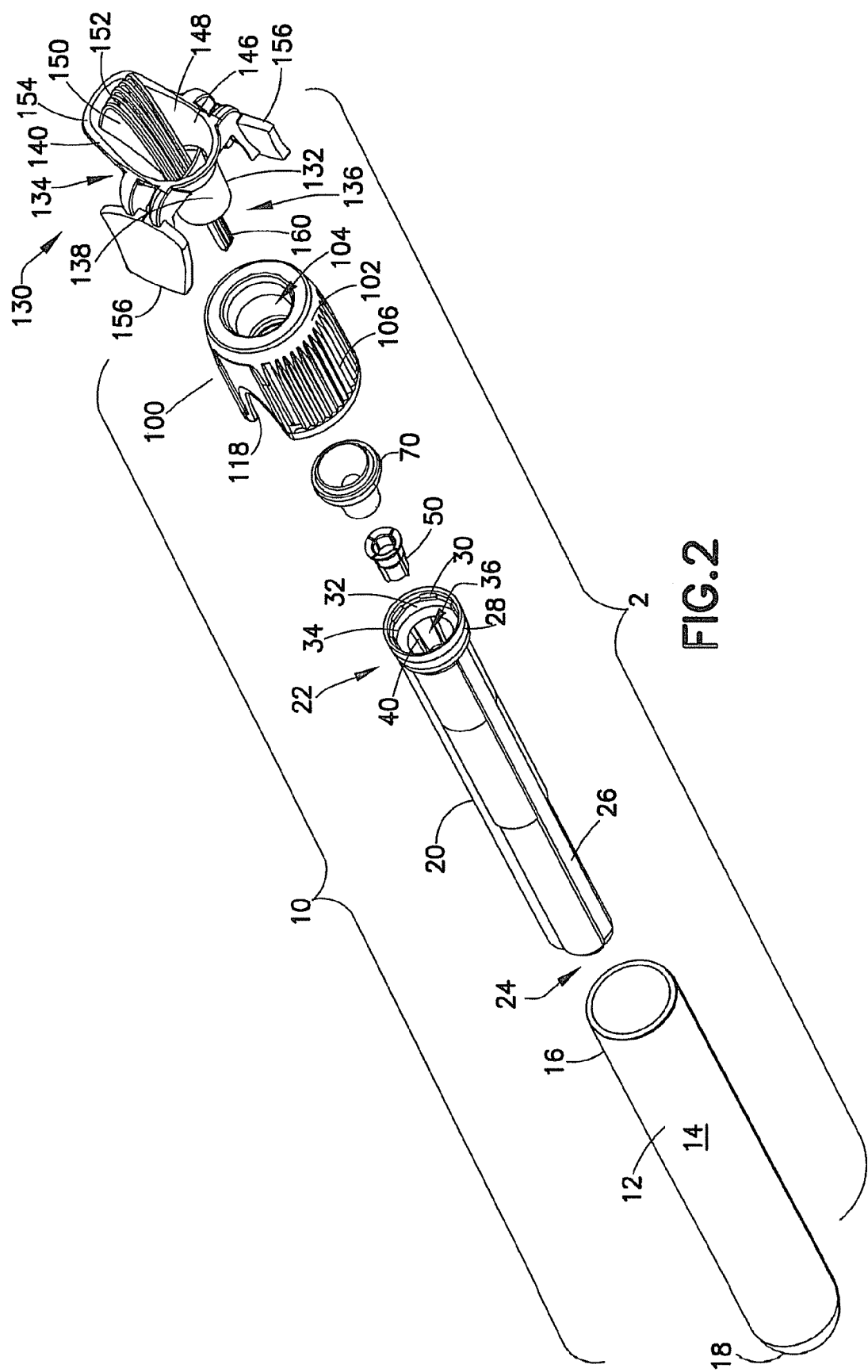
FIG. 2 is an exploded perspective view of the device shown in FIG. 1.

For purposes of the description hereinafter, spatial orientation terms, if used, shall relate to the referenced embodiment, device, component, or feature as it is oriented in the accompanying drawing figures or otherwise described in the following detailed description. However, it is to be understood that the embodiments, devices, components, or features described herein may assume many alternative variations. It is also to be understood that the specific embodiments, devices, components, and features illustrated in the accompanying drawing figures and described herein are simply exemplary and should not be considered as limiting.

Referring initially to FIGS. 1-4, a device 2 for collecting a fluid sample, such as a blood sample, is generally shown. Collection device 2 is an assembly of components, generally comprising a container assembly 10 and a collector 130 adapted to access the container assembly 10 and, further, guide fluid flow under capillary action into container assembly 10 as described herein. Container assembly 10 generally comprises a first or outer container 12, a second or inner container or member 20 disposed within outer container 12, an optional internal wall element 50 disposed in inner member 20, and a stopper or closure 70 for sealing outer container 12 and inner member 20. Wall element 50 may be associated with inner member 20 but is optional in the construction of container assembly 10 as described herein. A cap member 100 is associated with closure 70 to aid in handling of container assembly 10 and further assists closure 70 in sealing outer container 12 and inner member 20. As described herein, closure 70 and cap member 100 may be separate components or formed together as a combined structure. Outer container 12 may be any container or vessel capable of containing a fluid sample, typically a blood sample, therein, and is desirably in the form of a conventional blood collection tube or vessel. Outer container 12 may be constructed of any known material, such as glass or molded plastic material such as polyethylene terephthalate (PET). Outer container 12 is a generally cylindrical-shaped container having a sidewall 14 defining an open top end 16 and a closed bottom end 18. The closed bottom end 18 may have a rounded or arcuate shape as in the form of a conventional blood collection tube. Outer container 12 is sealed at the open top end 16 by closure 70, described herein, which is a pierceable or puncturable component formed of rubber or molded plastic material but may be made of any pierceable elastomeric material.

Figure 5:
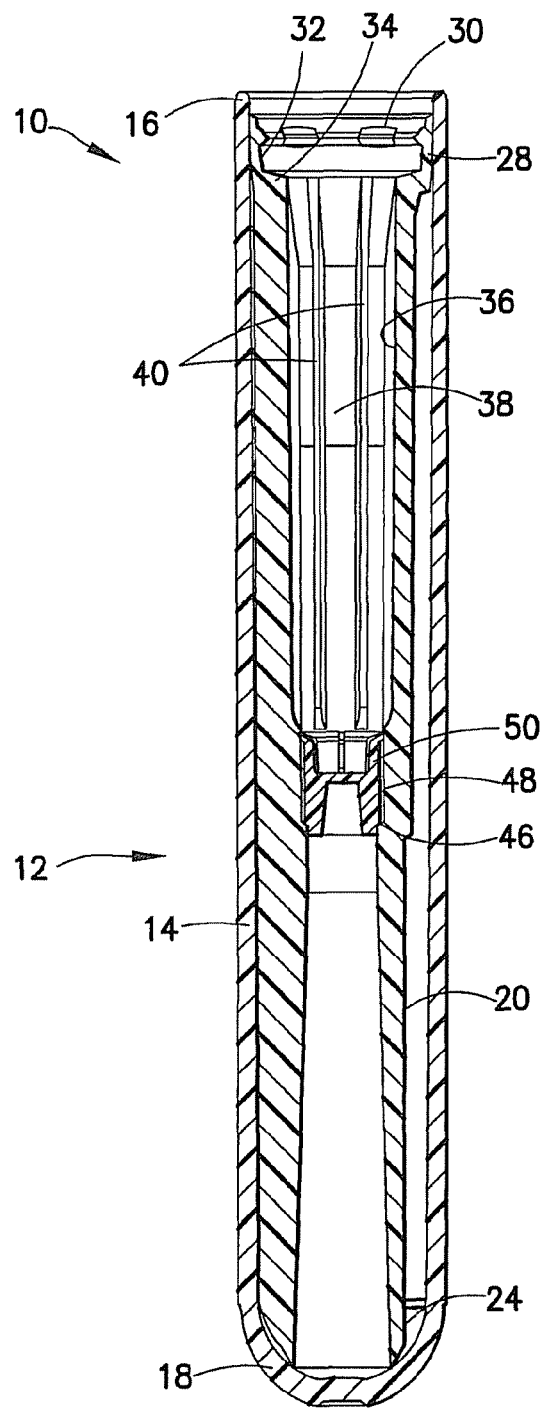
FIG. 5 is a cross-sectional view showing a partially assembled container assembly forming a part of the device shown in FIG. 1.
Figure 6:
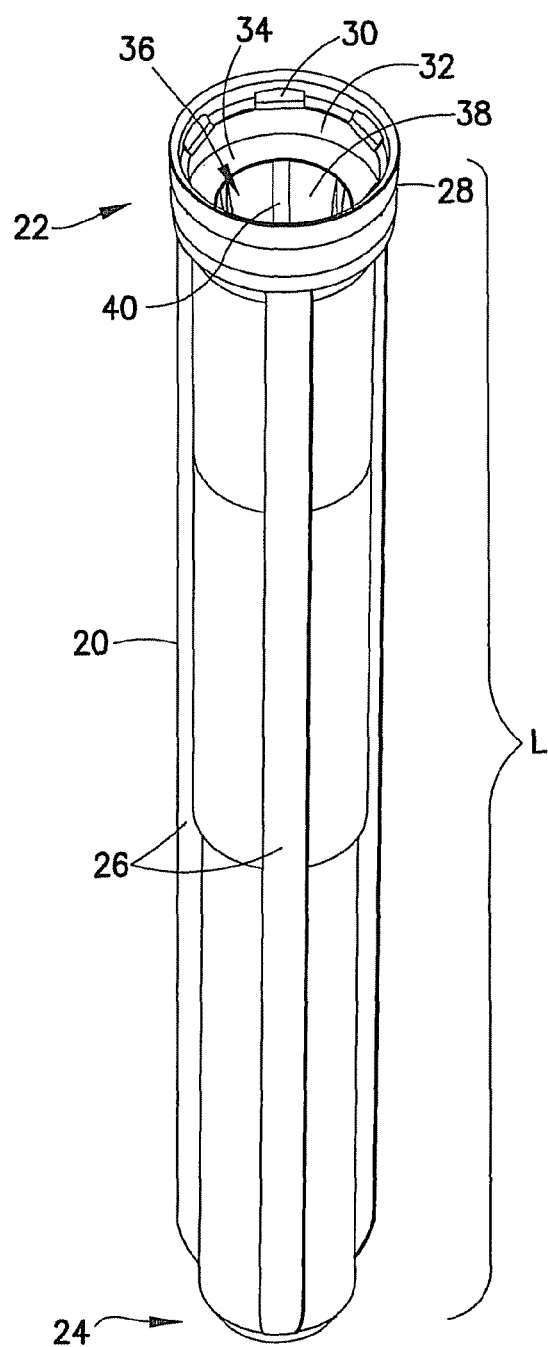
FIG. 6 is a perspective view of an inner member associated with the container assembly of FIG. 5.
Figure 7:
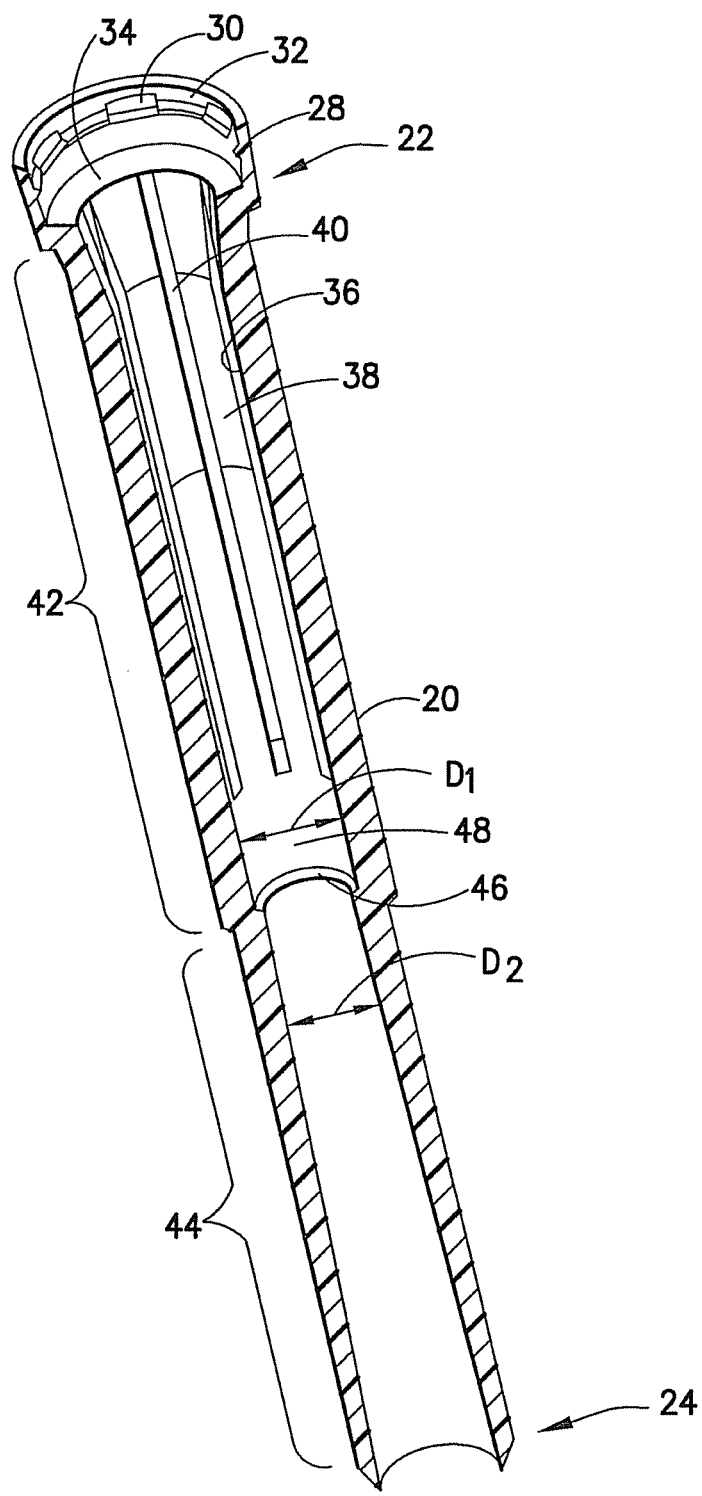
FIG. 7 is a longitudinal cross-sectional view of the inner member associated with the container assembly shown in FIG. 5.
Figure 8:
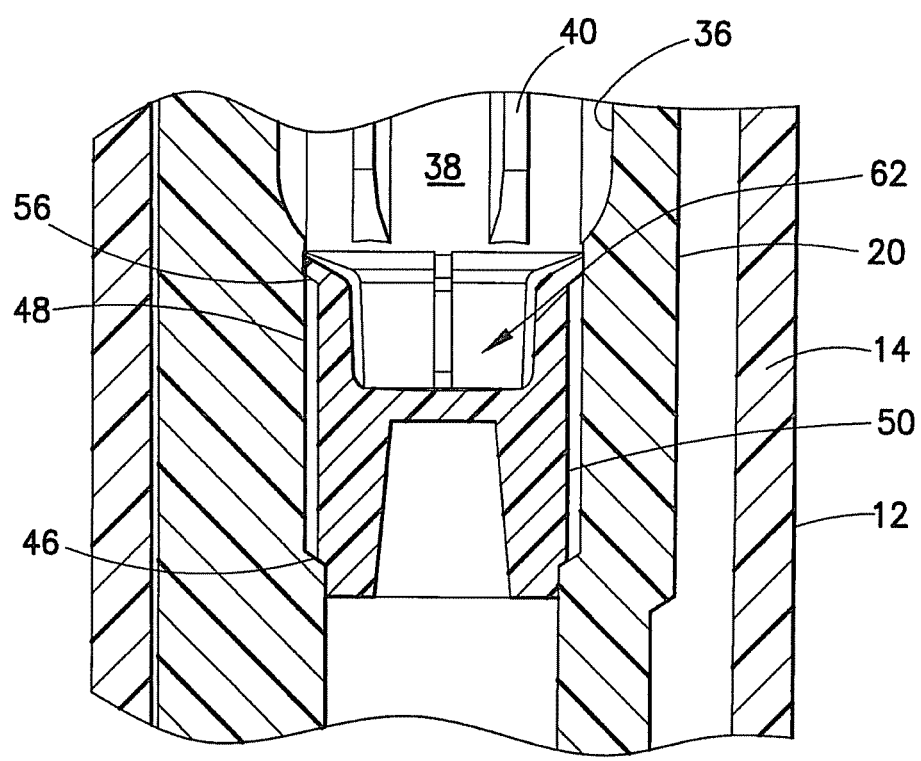
FIG. 8 is a detailed cross-sectional view showing the location of a wall element associated with the container assembly shown in FIG. 5.
Figure 9:
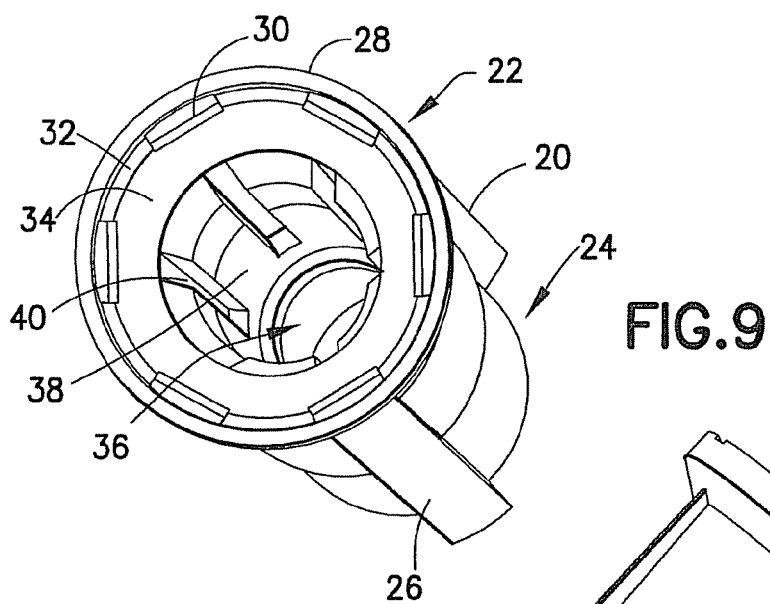
FIG. 9 is a top perspective view of the inner member associated with the container assembly shown in FIG. 5.
Figure 10:
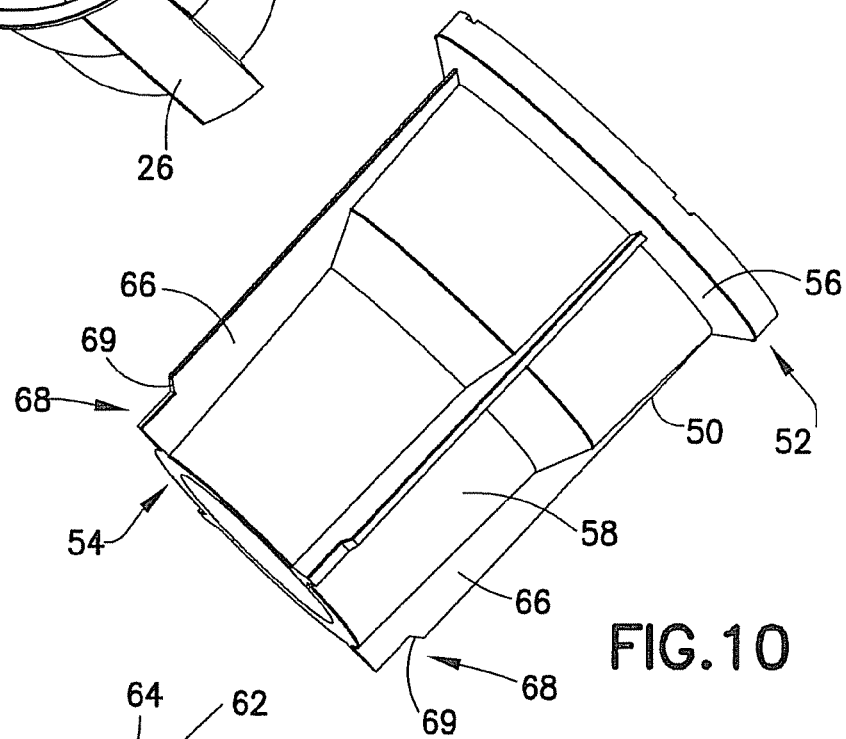
FIG. 10 is a perspective view of the wall element associated with the container assembly shown in FIG. 5.
Figure 11:
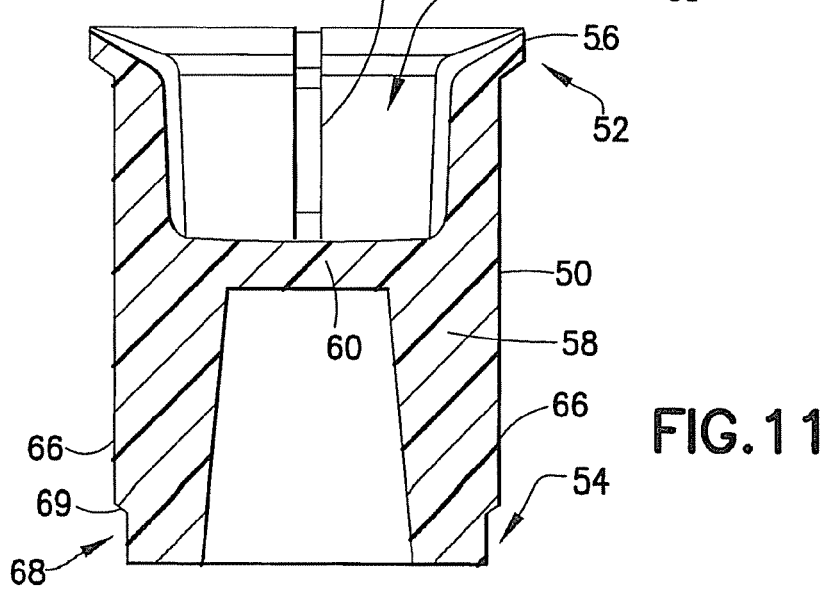
FIG. 11 is a longitudinal cross-sectional view of the wall element shown in FIG. 10.

Referring further to FIGS. 5-7, inner member 20 is a generally cylindrical or tubular body that is received within outer container 12 as illustrated. Inner member 20 is desirably disposed entirely within outer container 12. Inner member 20 has a first or proximal end 22 adjacent or proximate to the open top end 16 of outer container 12 and a second or distal end 24 adjacent or proximate to the closed bottom end 18 of outer container 12. Inner member 20 includes external longitudinal ribs or stabilizers 26 that extend substantially a length L of the inner member 20, desirably from a socket portion 28 formed at the first end 22 of inner member 20 to the second end 24 of inner member 20. Socket portion 28 forms a rim structure or lip at first end 22. The external ribs or stabilizers 26 are adapted to engage or contact the inner surface of sidewall 14 of outer container 12 and maintain the positioning of inner member 20 within outer container 12. The external ribs or stabilizers 26 may be segmented or non-continuous along the length L of inner member 20 if desired. Additionally, the external ribs or stabilizers 26 may be omitted if the outer periphery of inner member 20 is sized and shaped to be received within outer container 12 with minimal clearance therebetween and thereby generally contact the inner surface of sidewall 14 or outer container 12 around the entire outer periphery or circumference of the inner member 20. Socket portion 28 comprises a plurality of inward-extending retaining tabs 30 for interfacing with closure 70 as described herein. Socket portion 28 defines a vertical sidewall 32 and a recessed internal rim 34. As will be apparent from FIGS. 5-7, retaining tabs 30 may be provided on an inward projecting collar or rim structure formed on socket sidewall 32. Socket internal rim 34 is recessed in socket portion 28 and faces the open top end 16 of outer container 12. While retaining tabs 30 are desirably individual structures, a single continuous and desirably deflectable or deformable rib structure or shoulder may be provided in place of the illustrated retaining tabs 30.

Inner member 20 defines a central bore 36 that may extend completely through the inner member 20, or may extend partially therein. For example, a lower portion of inner member 20 may be a solid cylinder while the upper portion defines central bore 36. An inner surface 38 of the inner member 20 and defining bore 36 further includes or defines a plurality of capillary channels 40. Capillary channels 40 extend generally from socket portion 28 and, more particularly, from socket internal rim 34 downward in the inner surface 38 of inner member 20 to a bore diameter transition location or area described herein. Capillary channels 40 are desirably uniformly spaced around the periphery or circumference of bore 36 and are defined in the inner surface 38 of inner member 20 to extend in a longitudinal direction along the inner surface 38 of inner member 20. As illustrated, capillary channels 40 desirably extend only a portion of the length L of inner member 20 for reasons explained herein and are generally parallel in orientation. Inner member 20 is formed such that bore 36 exhibits differing diameters along the length L of inner member 20. In particular, bore 36 has a first internal diameter D1 at an upper area or portion 42 of inner member 20 and a second, smaller internal diameter D2 at a lower area or portion 44 of inner member 20. Thus, hollow or tubular inner member 20 has a first internal diameter D1 over an upper portion 42 of the inner member 20 and a second internal diameter D2 over a lower portion 44 of the inner member 20. An internal rim 46 is defined at a transition location between the first internal diameter D1 and second internal diameter D2 of bore 36. Internal rim 46 defines a demarcation location between the upper, larger diameter portion 42 and lower, smaller diameter portion 44 of inner member 20. A substantial portion of the lower portion of inner member 20 may be formed as a solid structure if desired. Capillary channels 40 are formed in the upper portion 42 of inner member 20. As shown in FIG. 7, for example, capillary channels 40 are formed in inner surface 38 of inner member 20 only in upper portion 42 of inner member 20. Thus, capillary channels 40 extend along only a portion of the inner surface 38 of inner member 20 in the upper portion 42. In particular, capillary channels 40 terminate a distance above internal rim 46 in bore 36 such that a receiving space or area 48 is defined for accommodating wall element 50. However, wall element 50, as alluded to previously, is optional. If desired, it may be omitted entirely or be provided as an integral part of inner member 20, for example, formed as a bottom wall extending across the inner member at the location of internal rim 46.

Figure 12:
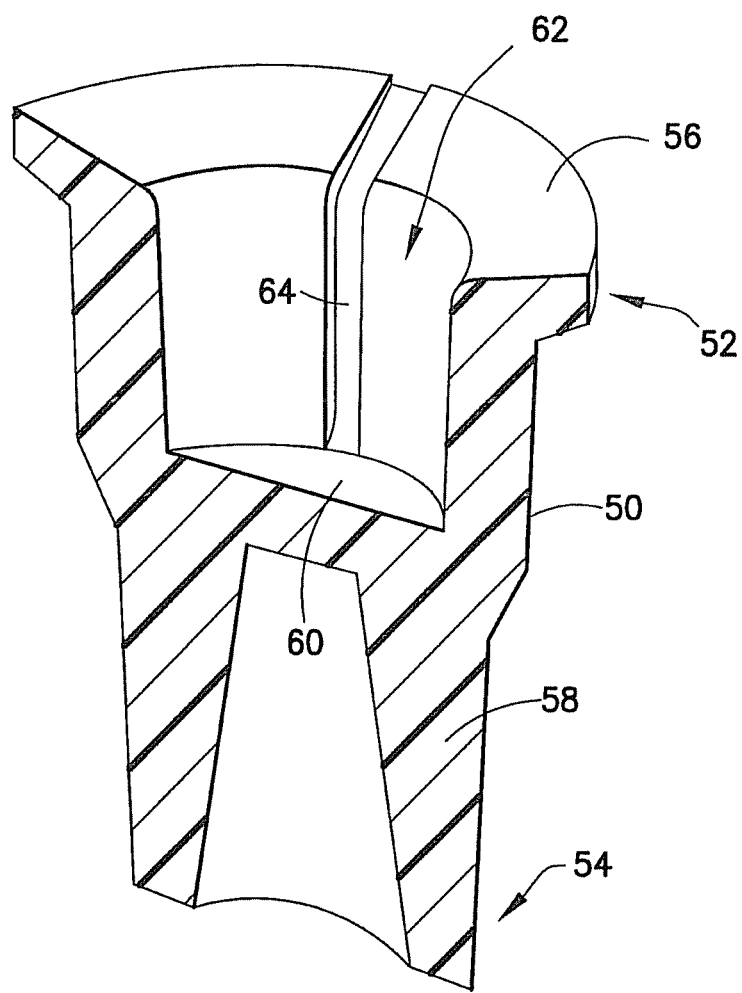
FIG. 12 is a second longitudinal cross-sectional view of the wall element shown in FIG. 10.
Figure 13:
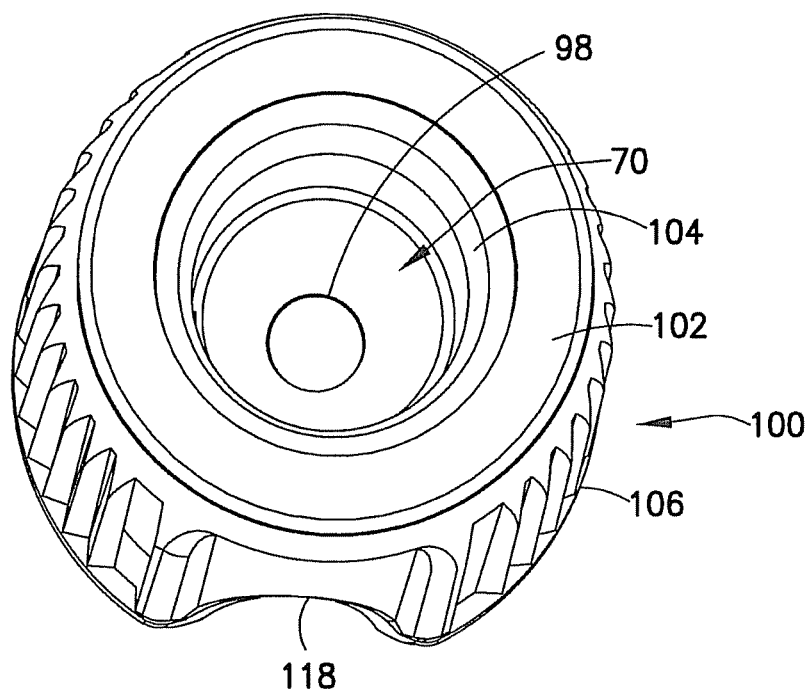
FIG. 13 is a top perspective view showing a closure and cap member used to seal the container assembly shown in FIG. 5.

Referring additionally to FIGS. 8-12, in an initial, "pre-centrifuge" state of container assembly 10, wall element 50 is disposed or situated in inner member 20 and located in the receiving space or area 48 associated with upper portion 42 of inner member 20. As described in the foregoing, receiving space or area 48 is an area of the bore 36 in inner member 20 that is located just below the terminus of capillary channels 40. While the operational use of wall element 50 is described fully herein, briefly, wall element 50 is intended in one embodiment to move downward in inner member 20 when container assembly 10 is exposed to centrifugal force in a conventional centrifuge machine thereby increasing the head space available in a volume defined above the wall element 50. Wall element 50 is formed in one embodiment as a generally cylindrical shaped body adapted to be received in central bore 36 of inner member 20 but may take other forms as described herein. In the depicted embodiment, wall element 50 has a first or upper end 52 and a second or lower end 54. As shown in FIG. 12, the upper end or portion 52 of wall element 50 has a larger diameter than the lower end or portion 54. The upper end 52 of wall element 50 defines an outward tapered or tapering rim 56 that is intended to contact the inner surface 38 of inner member 20 in bore 36 and, further, engage or contact the receiving area 48 in the upper portion 42 of bore 36 in inner member 20. Wall element 50 has a generally H-shaped cross-section along a vertical bisecting plane that is defined by a peripheral or circumferential sidewall 58 and a bisecting connecting wall 60. Sidewall 58 and bisecting wall 60 define a cup-shaped recess or cavity 62. A plurality of capillary channels 64 similar to capillary channels 40 in inner surface 38 of inner member 20 are defined by tapered rim 56 and sidewall 58 and extend downward along sidewall 58 to connecting or "bottom" wall 60. A plurality of external flanges 66 is provided on the outer side or surface of sidewall 58 and extend from outward tapered rim 56 downward to the bottom or second end 54 of wall element 50. As wall element 50 is intended to compress radially inward so as to "wedge" downward in inner member 20 during centrifuging, it is desirable that the body of the wall element 50 be made of a material sufficiently elastically deformable that radial inward flexing may result under centrifugal force. Desirably, this may also be accomplished by forming external flanges 66 to be sufficiently flexible or "deflectable" to allow the external flanges 66 to flex or compress radially inward toward a central axis C of wall element 50 under centrifugal forces typically present in conventional centrifuges used in medical applications. Accordingly, the external flanges 66 may be formed of a different material from the main body of wall element 50 if desired. Desirably, external flanges 66 each define a notch 68 with a tapered edge 69 that seats on the internal rim 46 defined in bore 36 in inner member 20. As centrifugal force acts on wall element 50, external flanges 66 deflect radially inward to unset the tapered edge 69 in each notch area 68 defined by the respective external flanges 66, allowing the wall element 50 to move or "wedge" downward in inner member 20 under the applied centrifugal force. While the external flanges 66 may alone deflect or compress radially inward, depending on the material comprising wall element 50, second or lower end 54 of wall element 50 may also exhibit some radial inward compression toward central axis C.

In summary, wall element 50 may be entirely omitted from container assembly 10 or may be provided as part of inner member 20 as described previously (for example, as a bottom wall) or, as described immediately above, may be provided as a separate component disposed in inner member 20. It is further optional for the wall member 50 to exhibit the wedging movement described immediately above and may be provided to set or define a collection volume in inner member 20 above the wall member 50. Accordingly, while wall member 50 has been described according to one compressive-type embodiment in the foregoing, it may take other forms such as a simple disc-shaped component, a cup-shaped component, and other forms, such as solid geometrical forms. In these latter forms, the wall member 50 may be spherical or cylindrical in shape as two non-limiting but possible forms for the wall member 50.

Figure 14:
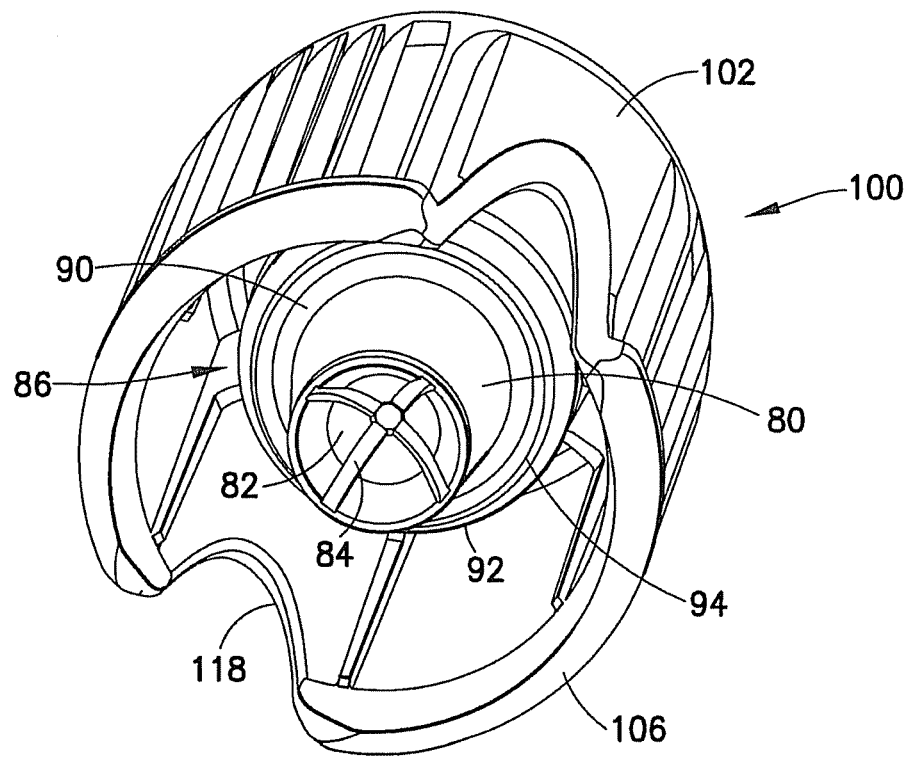
FIG. 14 is a bottom perspective view of the closure and cap member shown in FIG. 13.
Figure 15:
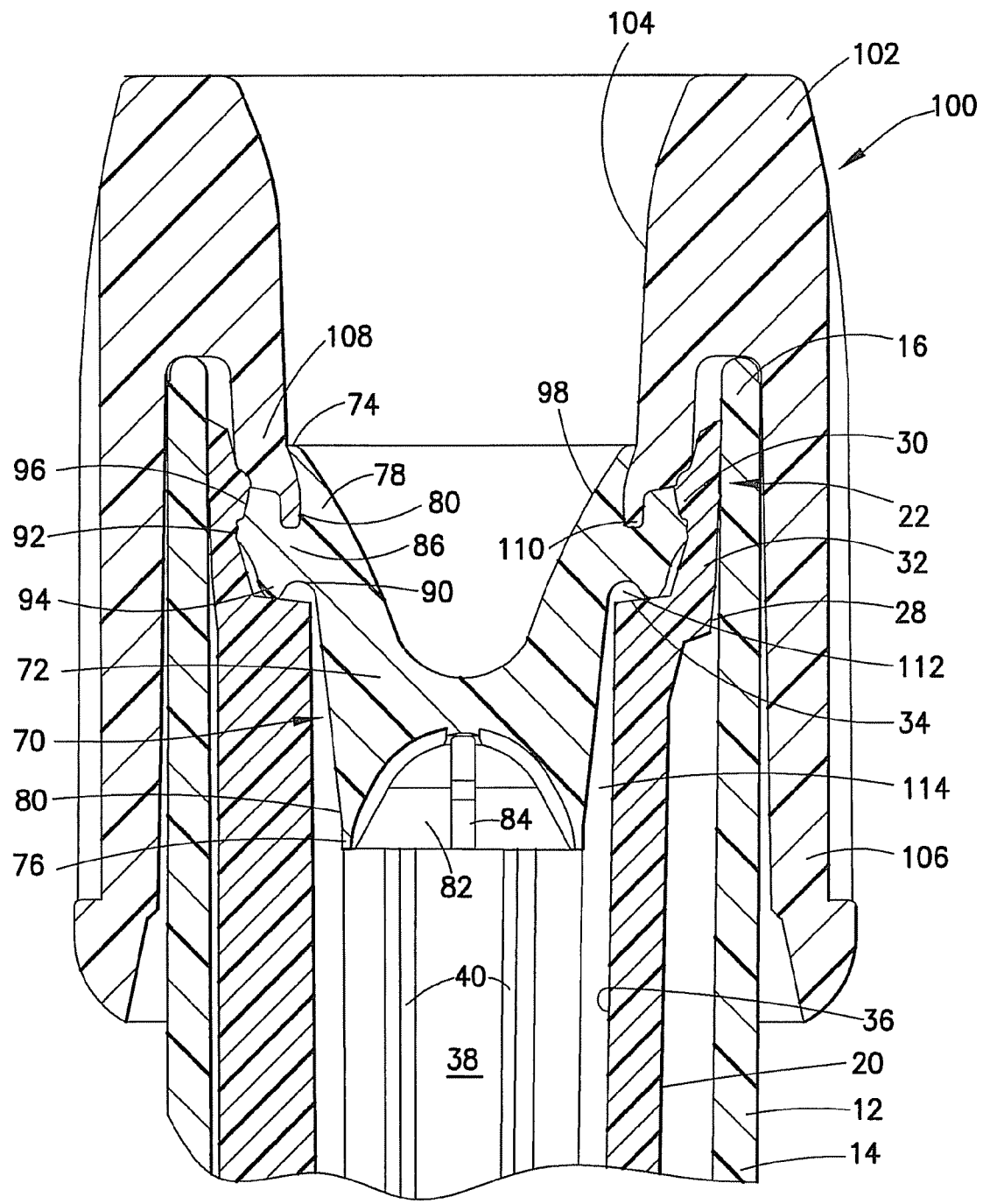
FIG. 15 is a cross-sectional view showing the association of the closure and cap member of FIGS. 13-14 with the container assembly shown in FIG. 5 and completing the assembly of the container assembly.

Referring to FIGS. 13-16, closure 70 is used to seal outer container 12 and inner member 20 from the exterior environment. If desired, outer container 12 may be in the form of a conventional blood collection tube or vessel that may be evacuated by conventional means. Thus, closure 70 may be adapted to interface with outer container 12 and, in particular, inner member 20 to maintain a vacuum condition in outer container 12. Closure 70 comprises a cylindrical closure body 72 having a first or proximal end 74 and a second or distal end 76. Closure body 72 further comprises an upward extending rim 78 forming first or proximal end 74 and a depending tapered portion 80. Depending tapered portion 80 generally tapers inward at a gradual angle. The distal end 76 of closure body 72 defines a distal recess or hollow area 82 which may generally be concave-shaped but also may take other configurations. As an example, distal recess 82 may be conical-shaped or take other similar formations as desired. A plurality of capillary channels 84 are formed or defined in distal recess 82. As shown in FIG. 14, for example, capillary channels 84 that extend outward and downward in distal recess 82 form an apex point in distal recess 82 to a circumferential or peripheral edge 85 formed by distal recess 82 at the distal end 76 of closure body 72. As further shown in FIG. 14, capillary channels 84 generally divide distal recess 82 into approximately 90° quadrants in one exemplary embodiment.

Figure 16:
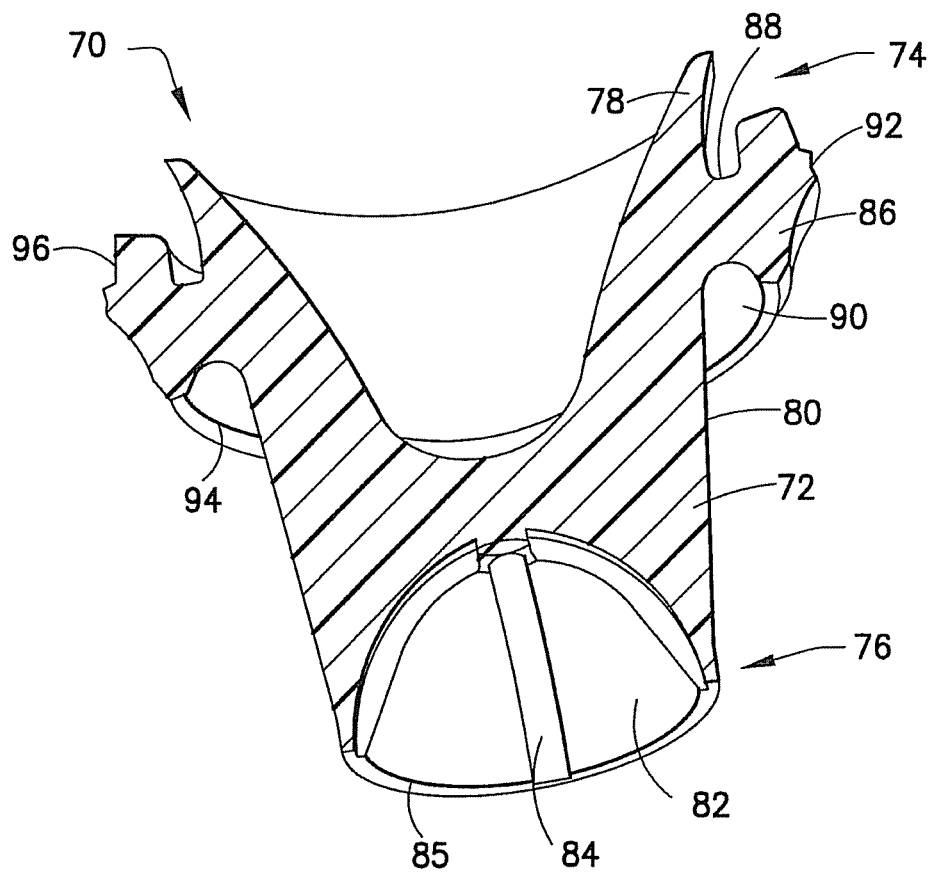
FIG. 16 is a longitudinal cross-sectional view of the closure used with the container assembly shown in FIG. 15.
Figure 17:
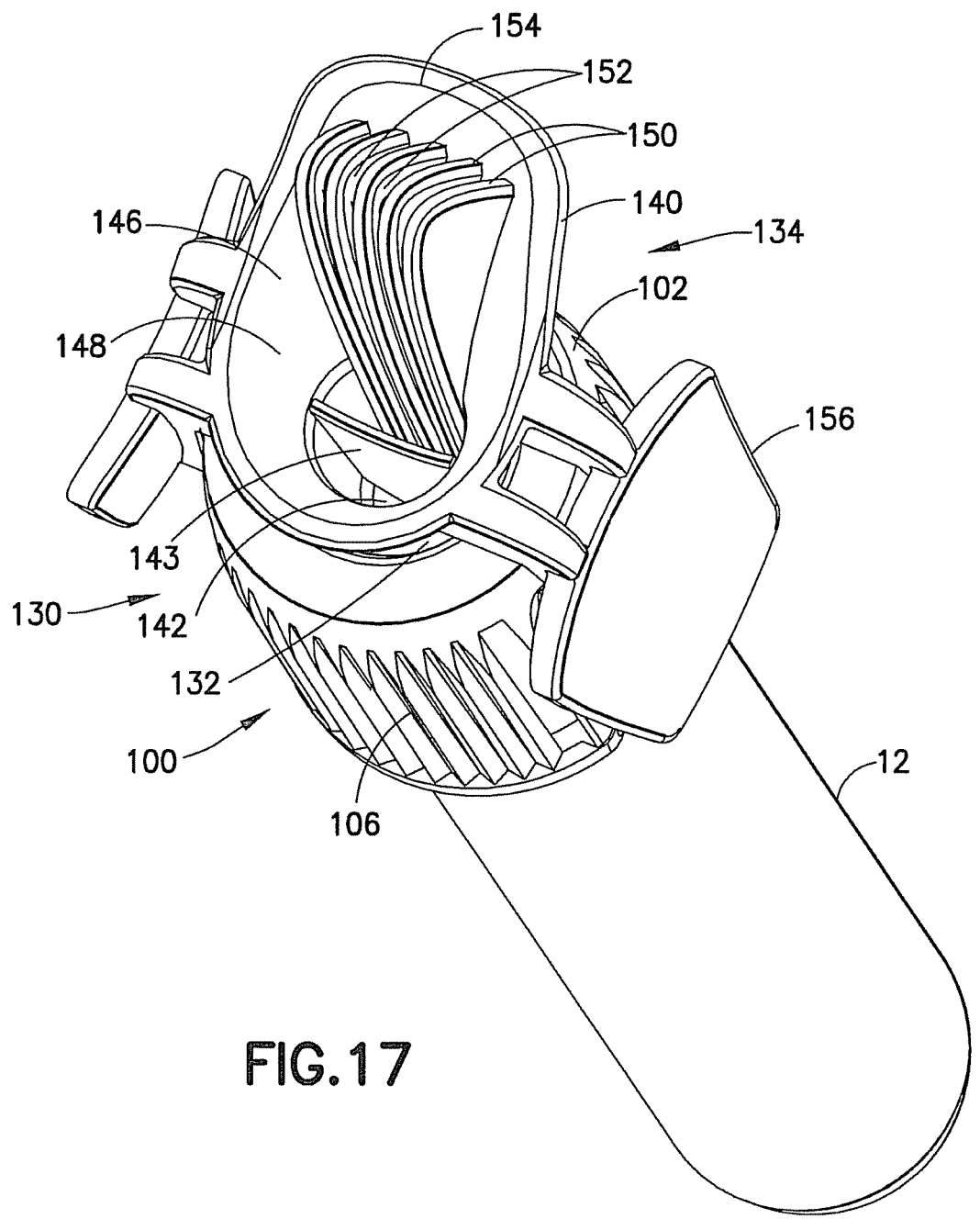
FIG. 17 is a top perspective view of the collection device shown in FIG. 1.

A collar or rim portion 86 extends radially outward from closure body 72 below upward extending rim 78. Collar portion 86 of closure body 72 defines upper, and lower, and generally opposed circumferential or peripheral grooves 88, 90. Collar portion 86 is formed with two generally orthogonally-orientated sealing shoulders, comprising a first sealing shoulder 92 and a second sealing shoulder 94. An engagement surface 96 is formed adjacent to first sealing shoulder 92 for interfacing with socket portion 28 of inner member 20. Moreover, the proximal end 74 of closure body 72 defines a proximal recess 98. As shown in FIG. 16, proximal recess 98 exhibits a generally concave-shape similar to distal recess 82 but may exhibit other shapes such as a generally conical-shape or possibly even a generally cylindrical-shape. Proximal recess 98 provides a location or area for accessing the outer container 12 via use of collector 130 described herein.

Briefly, however, collector 130 includes a puncturing or piercing element such as a puncturing needle cannula which is used to puncture closure 70 by inserting the puncturing element through closure body 72 in proximal recess 98. As noted previously, closure body 72 is made of pierceable rubber or other pierceable elastomeric material.

In one desirable combination, cap member 100 is generally adapted to interface with closure 70 to form a combined closure structure for sealing outer container 12 and inner member 20 from the exterior environment. Cap member 100 comprises a generally cylindrical body 102 that defines a central bore 104. Cap member 100 comprises an outer wall 106 that may be textured for facilitating handling by a user of container assembly 10. An inner wall 108 is spaced inward from outer wall 106 and terminates at a distal end with engagement rim 110. Engagement rim 110 is adapted to engage in a friction fit manner within upper circumferential groove 88 defined by collar portion 86 extending outward from closure body 72 of closure 70. Once closure 70 and cap member 100 are joined in the foregoing manner, the joined closure 70 and cap member 100 may be associated with outer container 12 and inner member 20 as described herein. However, it is also possible to first associate closure 70 with inner member 20 and thereafter associate cap member 100 with closure 70 in an alternative assembly process. Moreover, it may be desirable to form closure 70 and cap member 100 together into a single component that is assembled to inner member 20 and outer container 12. This may be accomplished, for example, by forming closure 70 and cap member 100 together in a two-shot molding process.

Assembled or joined closure 70 and cap member 100 are used to enclose and seal outer container 12 and inner member 20 by forming a sealing engagement between collar portion 86 associated with closure body 72 and socket portion 28 of inner member 20 and between the exterior of socket portion 28 of inner member 20 and the inner surface of the sidewall 14 of outer container 12. This double or dual sealing engagement is formed by inserting the tapered portion 80 of closure body 72 of closure 70 into the bore 36 defined by inner member 20 so that collar portion 86 is received within socket portion 28 of inner member 20. As collar portion 86 is received in socket portion 28, second sealing shoulder 94 is placed in engagement with socket internal rim 34 and first sealing shoulder 92 is placed in engagement with socket sidewall 32. As collar portion 86 is initially inserted into socket portion 28, the first sealing shoulder 92 engages retaining tabs 30 and pressure is applied downward so that the first sealing shoulder 92 slides past the retaining tabs 30 and the sealing engages socket sidewall 32 of socket portion 28. As collar portion 86 is received fully in socket portion 28 with second sealing shoulder 94 in engagement with socket internal rim 34 and first sealing shoulder 92 in engagement with socket sidewall 32, retaining tabs 30 engage the peripheral or circumferential engagement surface 96 on collar portion 86 to secure the engagement thereof in socket portion 28. In an alternative assembly process, closure 70 may be first associated with socket portion 28 of inner member 20 in which case collar portion 86 may deflect somewhat about upper circumferential groove 88 as the collar portion 86 is inserted into socket portion 28 until the first sealing shoulder 92 engages the socket sidewall 32 below retaining tabs 30 and the retaining tabs 30 engage engagement surface 96 on collar portion 86. Thereafter, engagement rim 110 may be inserted into the upper circumferential groove 88 defined by collar portion 86 as described previously.

Figure 3:
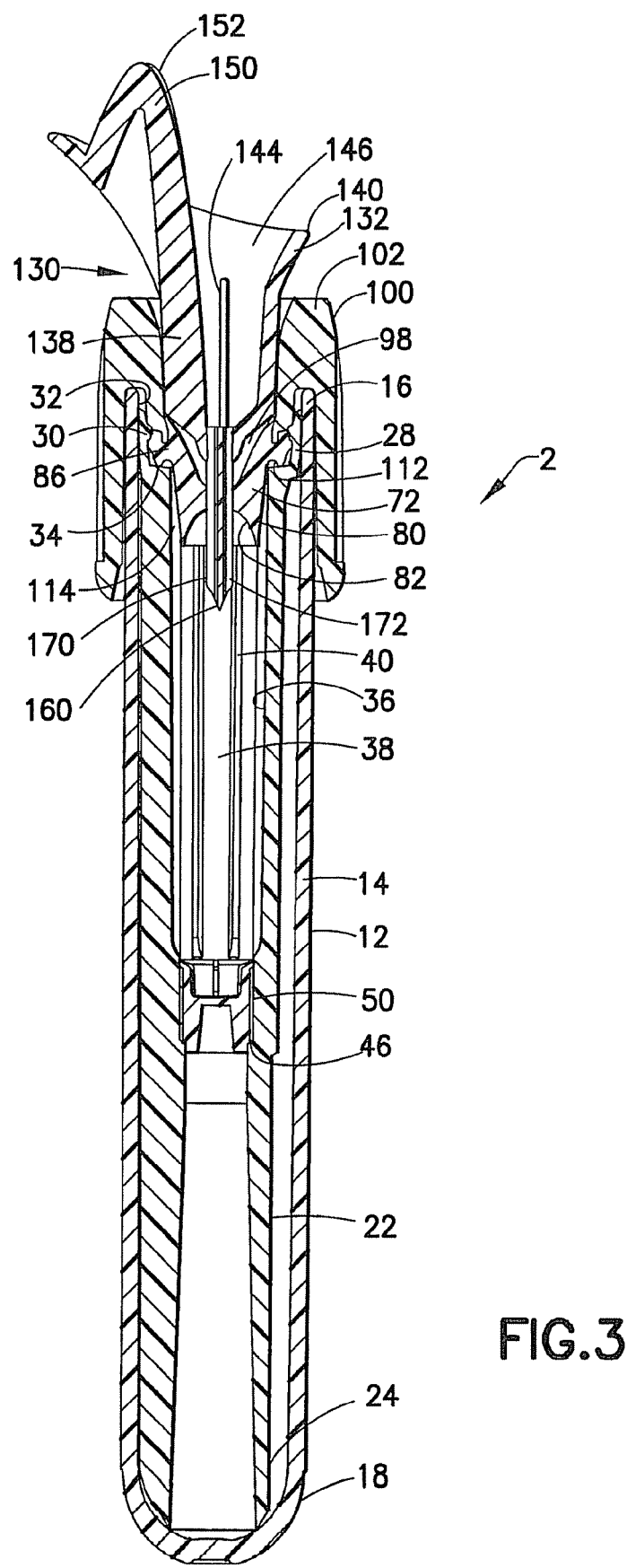
FIG. 3 is a cross-sectional view of the device taken along line 3-3 in FIG. 1.
Figure 3A:
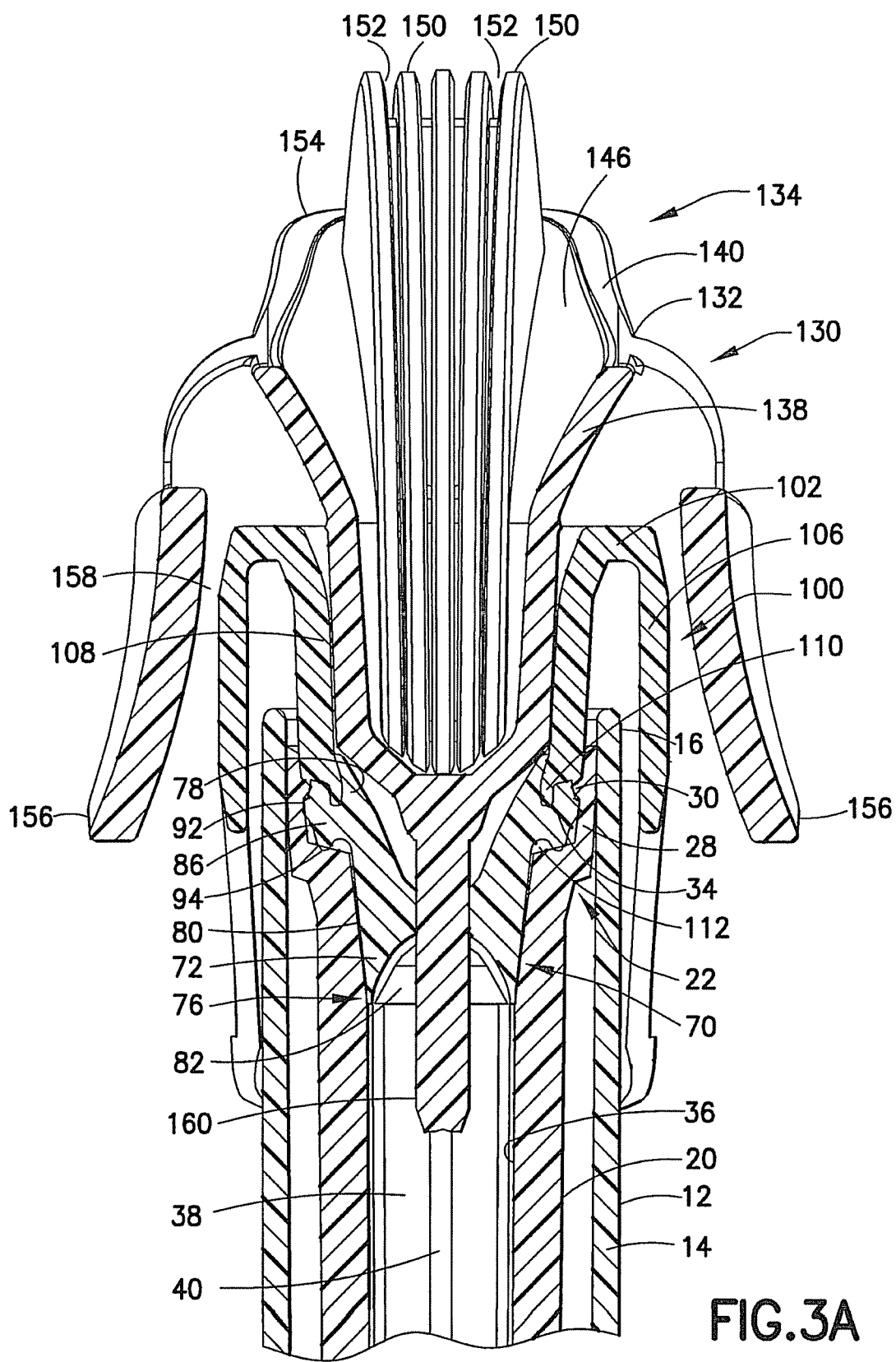
FIG. 3A is a partial cross-sectional view of the device taken along line 3A-3A in FIG. 1.
Figure 4:
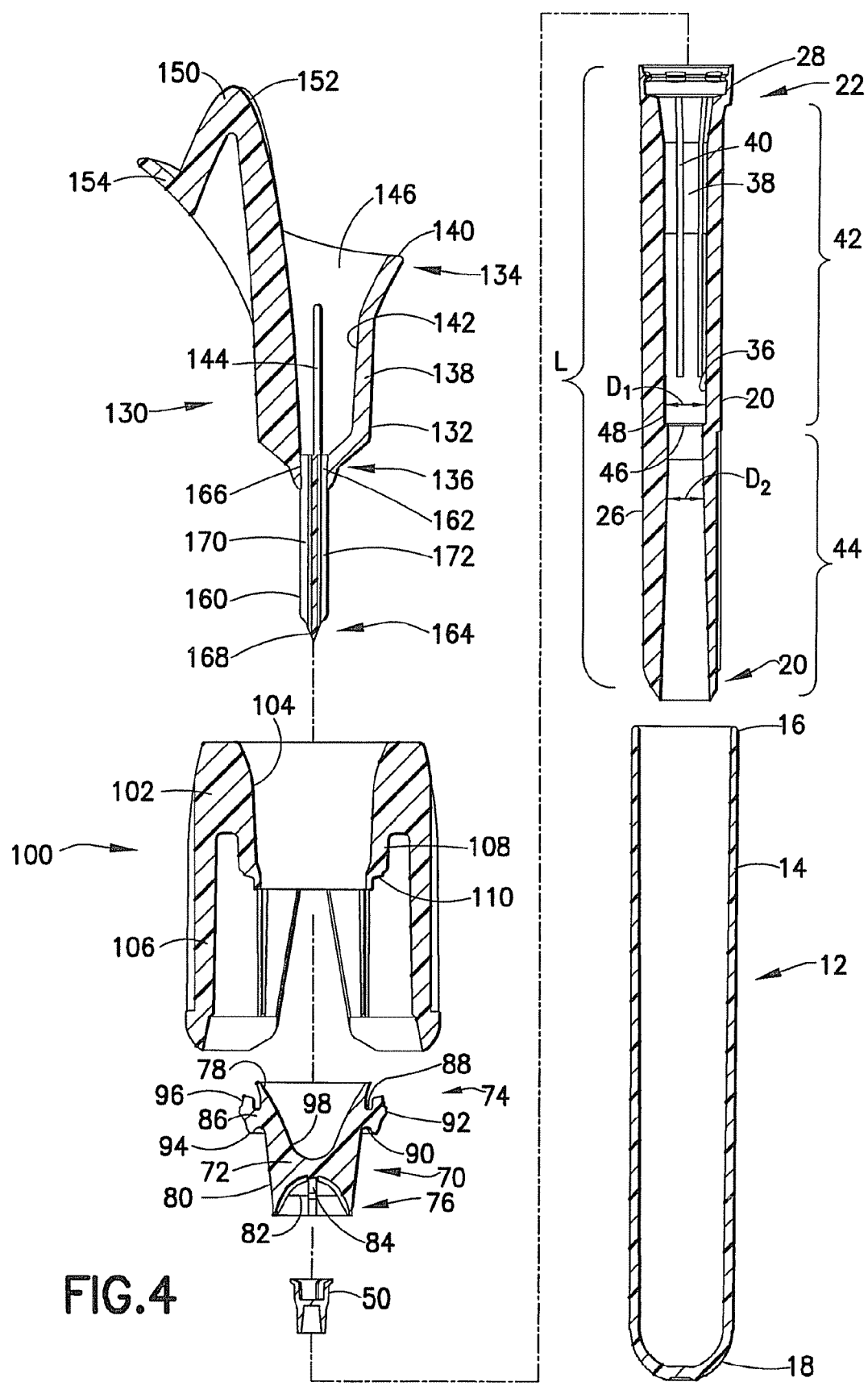
FIG. 4 is an exploded cross-sectional view of the device shown in FIG. 1.

Once closure 70 is associated with inner member 20, collar portion 86 exerts an outward force on socket portion 28 such that the exterior surface of socket sidewall 32 presses against the inner surface of sidewall 14 of outer container 12 forming a generally fluid tight seal therebetween. A similar generally fluid tight seal is provided by the engagement of first sealing shoulder 92 on collar portion 86 and the inner surface of socket sidewall 32. The dual engagement of second sealing shoulder 94 against socket internal rim 34 and first sealing shoulder 92 against the inner surface of socket sidewall 32 provides redundancy in the seal between collar portion 86 and socket portion 28. Typically, the former engagement of second sealing shoulder 94 against socket internal rim 34 forms the primary fluid seal while the latter engagement of the first sealing shoulder 92 against the inner surface of socket sidewall 32 provides a secondary fluid seal. However, these engagements have additional advantages as well. As described previously, second or bottom circumferential groove 90 is formed opposite from top circumferential groove 88 by collar portion 86. Once the second sealing shoulder 94 is seated against socket internal rim 34 of socket portion 28, an annular cavity 112 is defined by bottom circumferential groove 90 and the socket internal rim 34. This "first" annular cavity 112 is in fluid communication or connection with a second annular cavity 114 defined between the tapered external surface of tapered portion 80 of closure body 72 and the inner surface 38 of inner member 20 in bore 36. These fluidly-connected cavities 112, 114 may be used to provide a visual indication to a user of collection assembly 10 when a fluid sample, typically blood, has reached a maximum fill volume for the container assembly 10. As will be appreciated from FIG. 15, for example, with closure 70 associated or engaged with inner member 20, an enclosed fluid sample chamber 116 is defined within container assembly 10. Fluid sample chamber 116 is generally bound or defined by the inner surface 38 of inner member 20, bisecting or interconnecting wall 60 of wall element 50, and collar portion 86 of closure body 72. This fluid sample chamber 116 is accessible via use of collector 130 as described herein and as illustrated in FIG. 3. It will be clear from FIG. 15, for example, that capillary channels 84 in distal recess 82 of closure body 72 are located in proximity to capillary channels 40 in the inner surface 38 of inner member 20 but need not directly connect to capillary channels 84 for fluid flow under capillary action to pass from capillary channels 84 to capillary channels 40 as the distal circumferential edge 85 of taper portion or barrel 80 of closure body 72 provides a sufficient access route or edge for a capillary fluid sample to pass outward to the inner surface 38 of inner member 20 and enter capillary channels 40 therein.

With closure 70 associated or engaged with inner member 20 as described hereinabove, cap member 100 is positioned such that outer wall 106 of cap member 100 extends downward over the exterior of sidewall 14 of outer member 12 and may be grasped by a user of container assembly 10. Cutouts 118 may be provided in opposing sides of outer wall 106 of cap member 100 so that the visual-indication fill feature provided by interconnecting annular cavities 112, 114, described previously, is available for external inspection to a user of container assembly 10. Such visual inspection is made by viewing the tapered portion 80 of closure body 72 of closure 70 through sidewall 14 of outer container 12. For such visual fill indication to be apparent to the user, inner member 20 is made of similar material as outer container 12 such as a molded clear plastic material. This visual-indication fill feature is akin to a flash chamber known in the medical field in blood collection applications and is described further herein.

Referring further to FIGS. 17-21, an embodiment of collector 130 used to gain access to fluid sample chamber 116 and, further, direct or collect a bodily fluid sample such as blood under capillary action into fluid sample chamber 116 is shown. In this embodiment, collector 130 comprises a generally tubular-shaped body 132 comprising a first or proximal end 134 and a second or distal end 136 and an annular sidewall 138 extending therebetween. The proximal end 134 comprises a rim portion 140 that generally tapers outward from collector body sidewall 138 at the first or proximal end 134 of collector body 132. Collector body sidewall 138 defines a central bore 142 extending through the collector body 132. As shown, for example, in FIG. 17, a central wall or divider 144 extends across bore 142 between opposed sides of sidewall 138. An inner surface of collector body 132 defining bore 142 optionally defines a plurality of longitudinally-extending capillary channels (not shown). If provided, at least two capillary channels are defined in bore 142 defined by sidewall 138 of collector body 132, typically at least on opposed sides of bore 142. An inner surface 146 of rim portion 140 has a generally curved or arcuate shape and rim portion 140 generally defines a concave, cup-shaped collector area or recess 148. Collector area or recess 148 forms an expanded area or volume where, for example, a patient may place his or her fingertip after being pricked with a lancet or other device so that a blood sample may be taken under capillary action. Central divider or wall 144 prevents the patient from inserting his or her fingertip fully into bore 142. Collector area or recess 148 is also adapted, as described herein, for collecting a capillary sample of fluid and directing the same into central bore 142 defined by collector body 132.

A series or plurality of channel members 150 is desirably present on collector body 132 and, in particular, on rim portion 140 and sidewall 138 of collector body 132. Channel members 150 extend along the inner surface 146 of rim portion 140 and desirably extend downward into and through central bore 142 defined by sidewall 138 to terminate approximately at the distal end 136 of collector body 132. Channel members 150 are spaced apart to define intervening capillary channels 152 which are approximately parallel to one another. A further feature of rim portion 140 is that the rim portion 140 may comprise an upward and generally outward extending rear wall or flange 154. Rear wall or flange 154 tapers outward in a generally similar manner to rim portion 140 but extends further laterally outward as well as upward from rim portion 140. Rear wall or flange 154 may be used to visually guide a user of collector 130 in placing a patient's fingertip into rim portion 140. Channel members 150 in the embodiment illustrated generally bulge upward from rim portion 140 and, particularly, upward from rear wall 154. The bulged form of channel members 150 has several functions but is primarily provided to guide insertion of a patient's fingertip into rim portion 140. However, the steepness of the capillary channels 152 due to the bulged shape of channel members 150 has advantages in increasing the potential energy available to cause capillary action fluid flow in the capillary channels 152.

Figure 18:
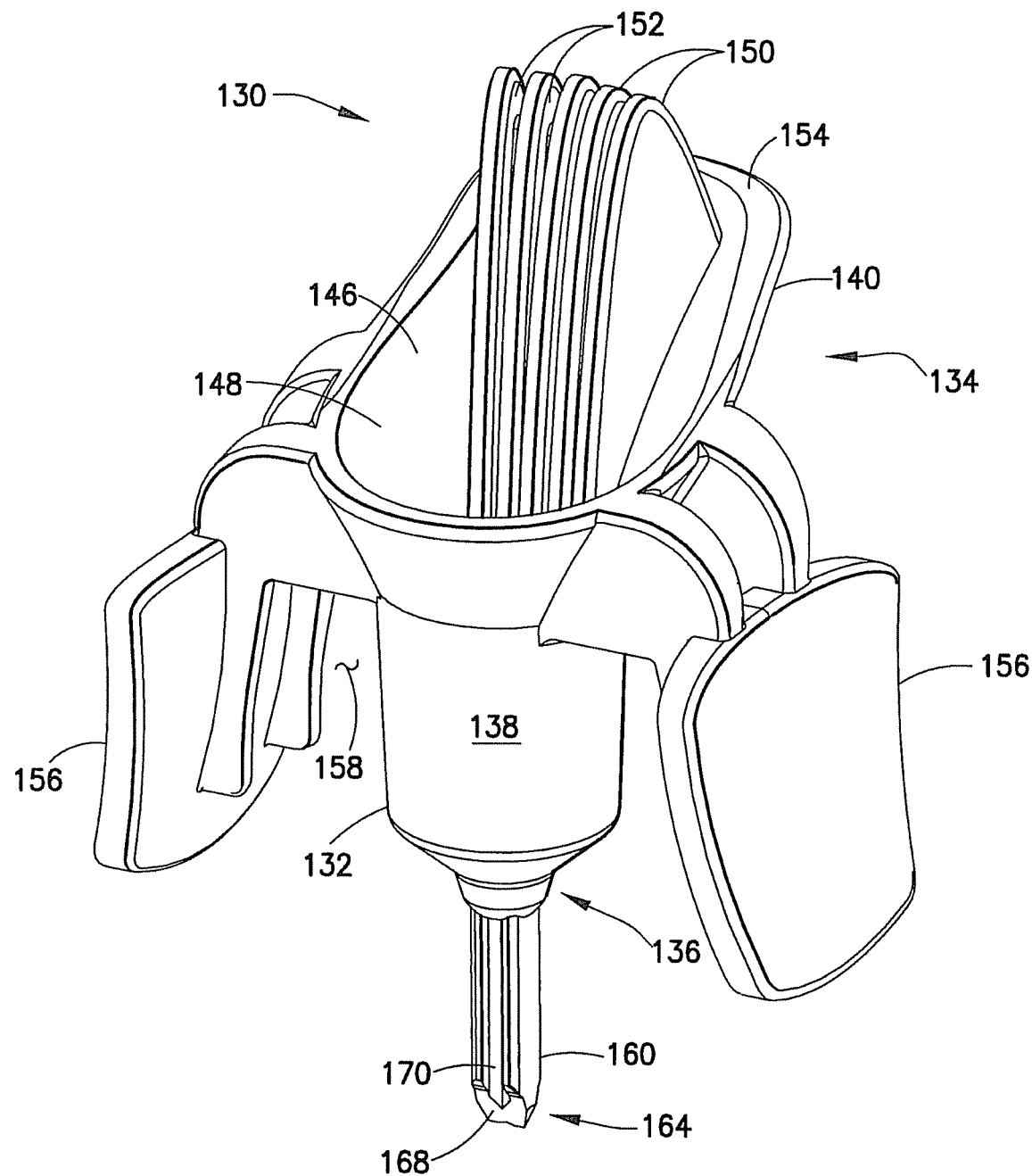
FIG. 18 is a front perspective view showing a collector used with the collection device shown in FIG. 1.

Channel members 150 and, more particularly, intervening capillary channels 152 form capillary flow channels to guide a fluid sample downward into central bore 142 defined by sidewall 138 of collector body 132 under capillary action. Thus, capillary channels 152 operate generally as fluid guides to guide a desired fluid sample into central bore 142 in collector body 132. It will be appreciated from FIG. 3 discussed previously, that an outer diameter of sidewall 138 of collector body 132 is slightly smaller than an inner diameter of the inner wall 108 of cap member 100 so that collector body 132 may be inserted into central bore 104 of the body 102 of cap member 100. Finger tabs 156 may extend outward and downward from rim portion 140 and extend downward along the outer side or surface of collector body 132 to provide locations for the user of collector 130 to place his or her fingers. Surface texturing may be provided on finger tabs 156 if desired for ergonomic purposes. As shown in FIG. 18, an annular area 158 is defined between finger tabs 156 and the outer surface of sidewall 138 which is sized large enough to accommodate the radial thickness of the body 102 of cap member 100 between the outer wall 106 and inner wall 108 thereof.

Figure 19:
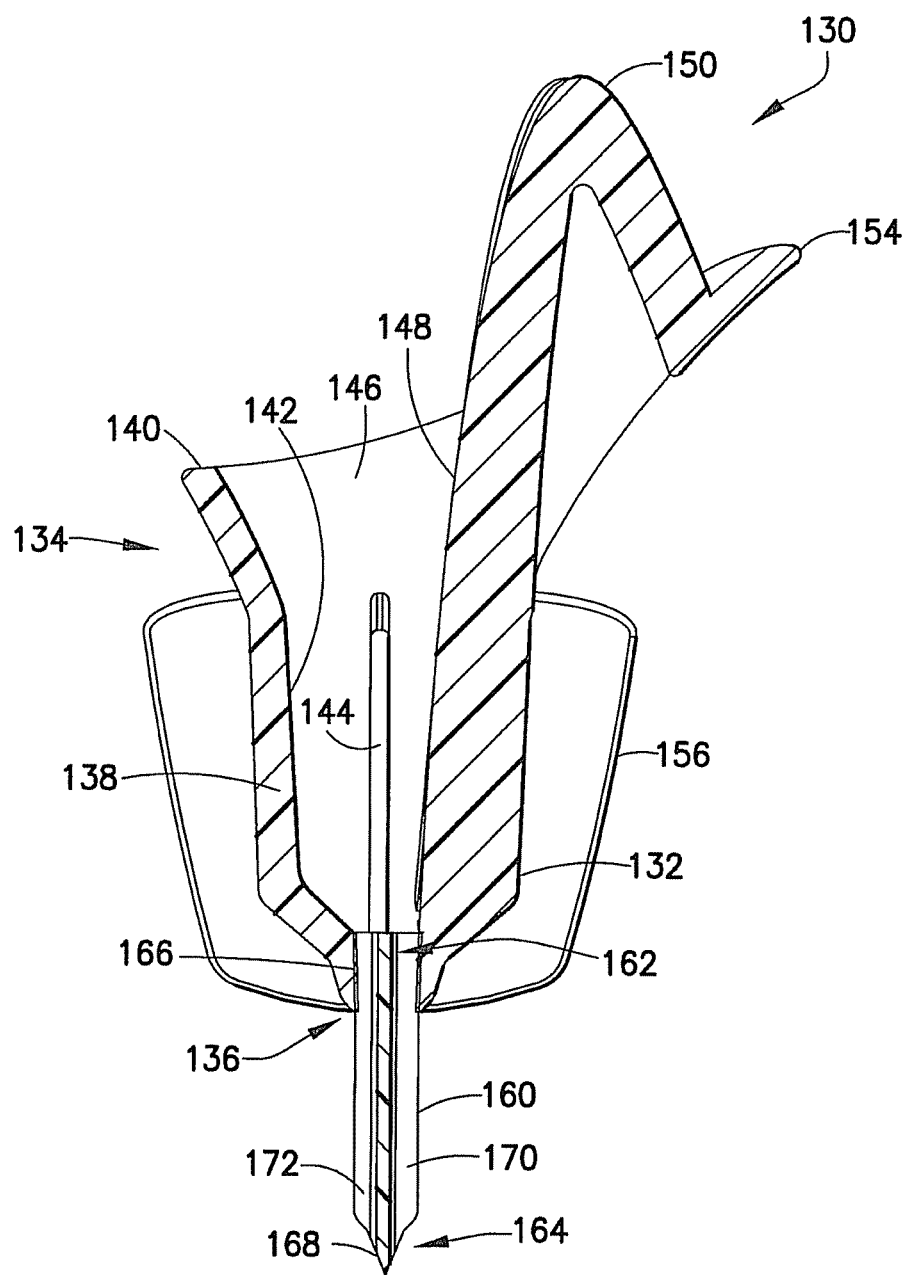
FIG. 19 is a longitudinal cross-sectional view of the collector shown in FIG. 18.
Figure 21:
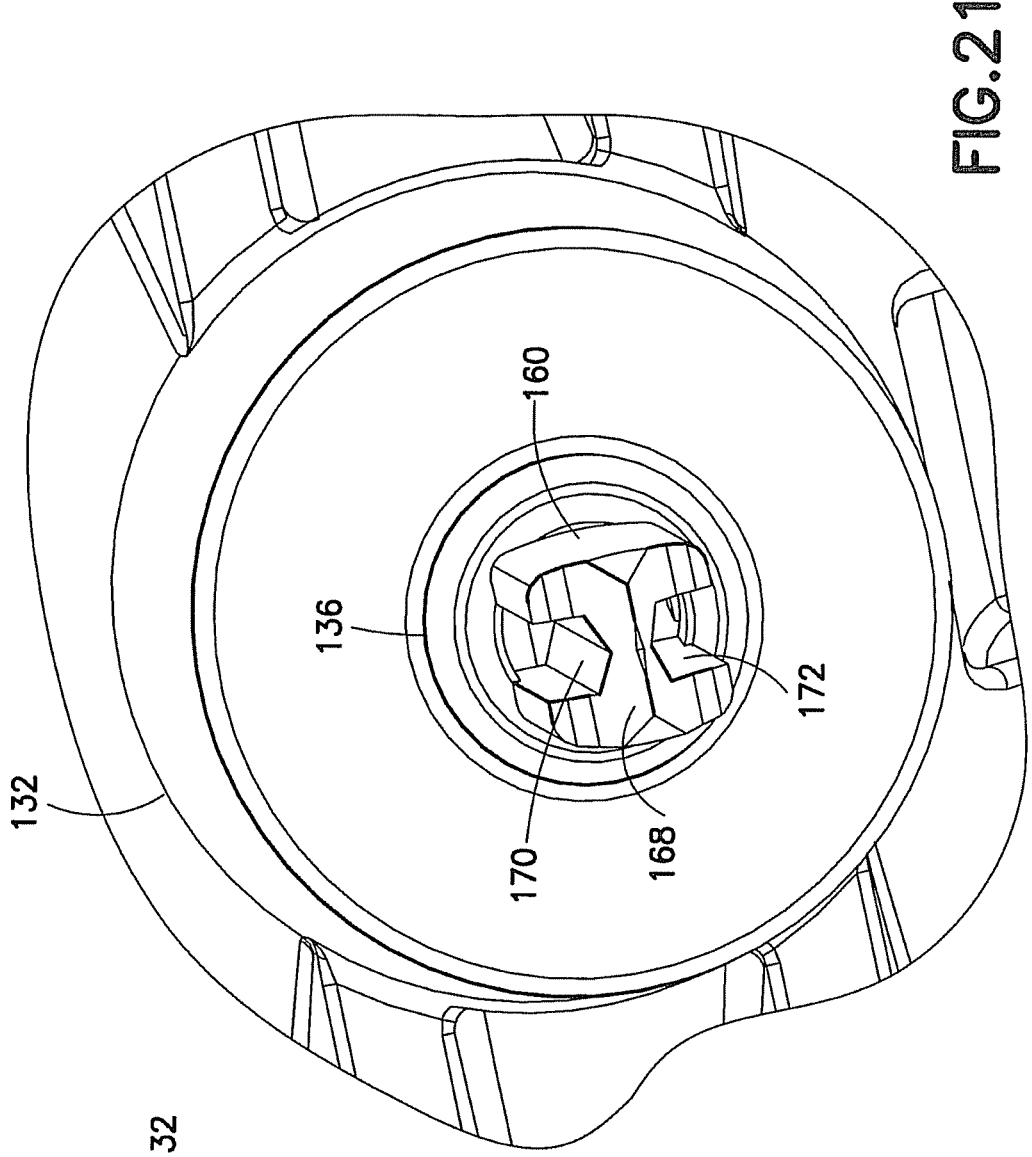
FIG. 21 is another perspective view of the distal end of the collector shown in FIG. 18 showing features of the penetrating needle cannula of the collector.
Figure 20:
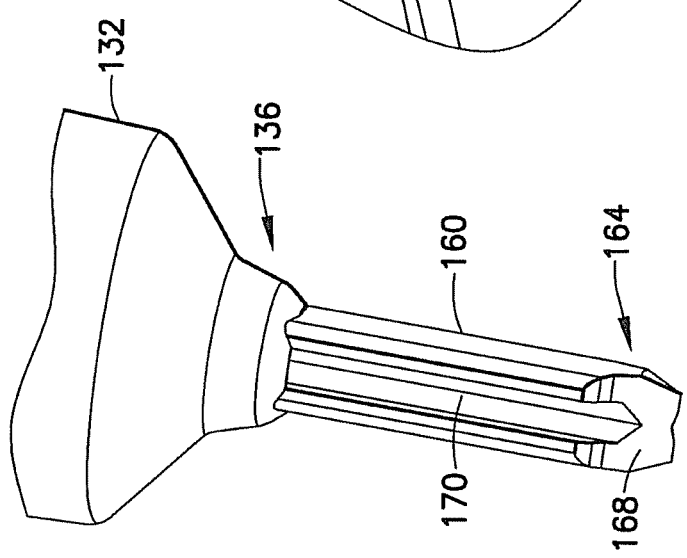
FIG. 20 is a perspective view of a distal end of the collector shown in FIG. 18 showing features of a penetrating needle cannula of the collector.

Another feature of collector 130 is the provision of an accessing needle cannula 160 at the distal end 136 of collector body 132 used to pierce or puncture closure body 72 to gain access to the interior of container assembly 10 and, particularly, fluid sample collection chamber 116. Puncturing or penetrating needle cannula 160 comprises a first or proximal end 162 and a second or distal end 164. The proximal end 162 of penetrating needle cannula 160 is disposed in a receiving recess 166 defined in collector body 132 at distal end 136. The proximal end 162 of penetrating needle cannula 160 may be secured in receiving recess 166 by conventional means in the medical art such as by medical grade adhesive and like securing techniques. Penetrating needle cannula 160 may alternatively be formed integral with collector body 132 of collector 130. Penetrating needle cannula 160 has a generally H-shaped transverse cross section and terminates in a generally flat-faced needle point 168 which is suited to puncturing closure body 72 of closure 70. Due to the H-shape of the cross-section of penetrating needle cannula 160, two opposed and longitudinally extending channels 170, 172 are defined in penetrating needle cannula 160. Channels 170, 172 extend the length of penetrating needle cannula 160 and, as shown in FIG. 19, for example, terminate at the proximal end 162 of penetrating needle cannula 160. While not immediately apparent from FIG. 21, for example, capillary channels may have different diameters so that one channel may operate as a fluid conduction capillary channel 172 while the second channel may operate as a vent channel or conduit 170 to atmospheric pressure when penetrating needle cannula punctures closure body 72 of closure 70 during use. Central divider or wall 144, in addition to the previously discussed purpose of limiting finger insertion into bore 142, is present for the purpose of dividing or separating channels 170, 172 for the two distinct functions identified in the foregoing. The upper termination point of dedicated capillary channel 172 is located in close proximity to the distal terminus of capillary channels 152 defined by channel members 150 on collector body 132. In this regard, once a fluid sample has accumulated in capillary channels 152, a generally seamless capillary action fluid flow path is present through to the distal end 136 of penetrating needle cannula 160.

Figure 24:
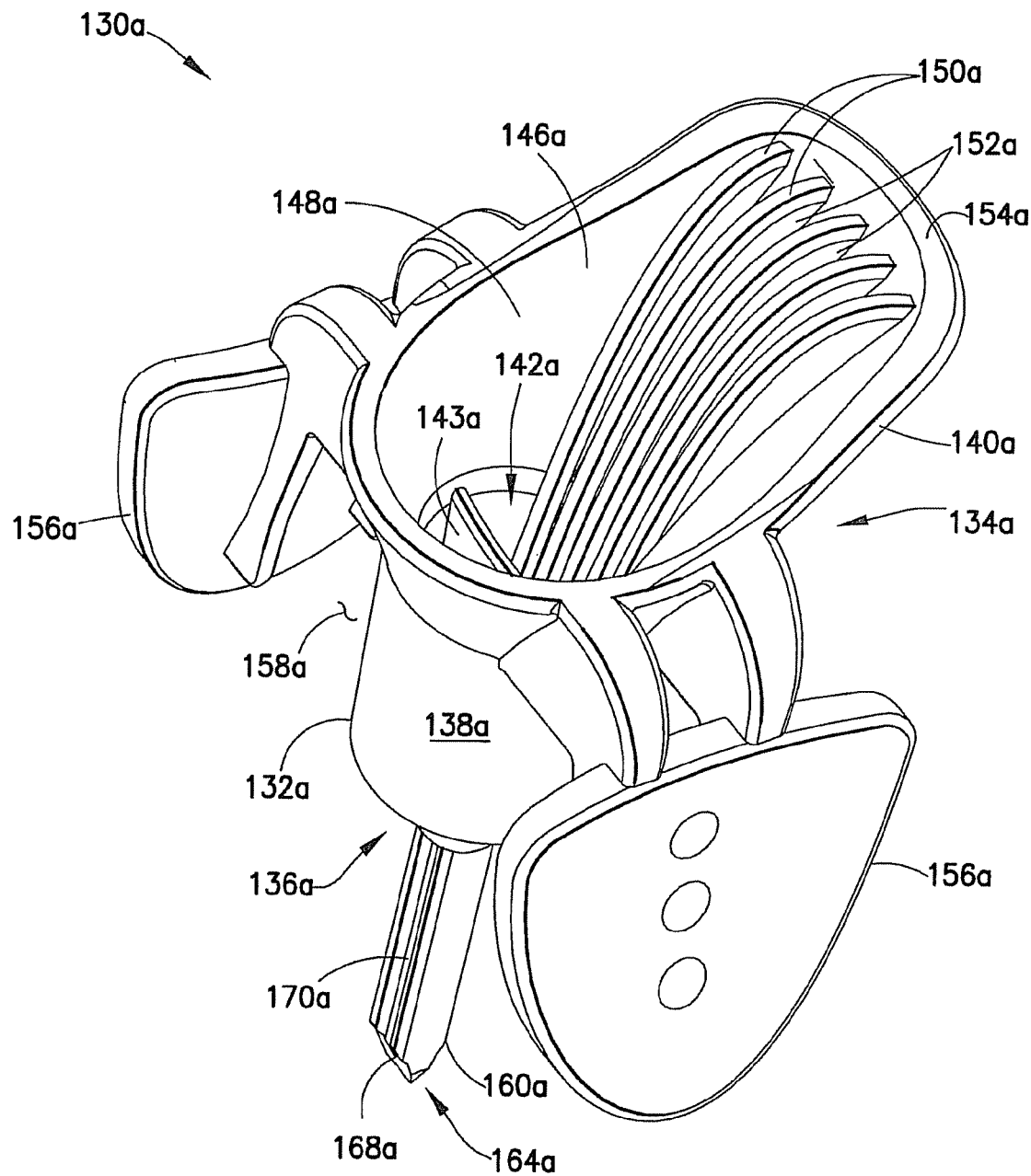
FIG. 24 is a top perspective view of another embodiment of the collector optionally used with the collection device shown in FIG. 1.
Figure 25:
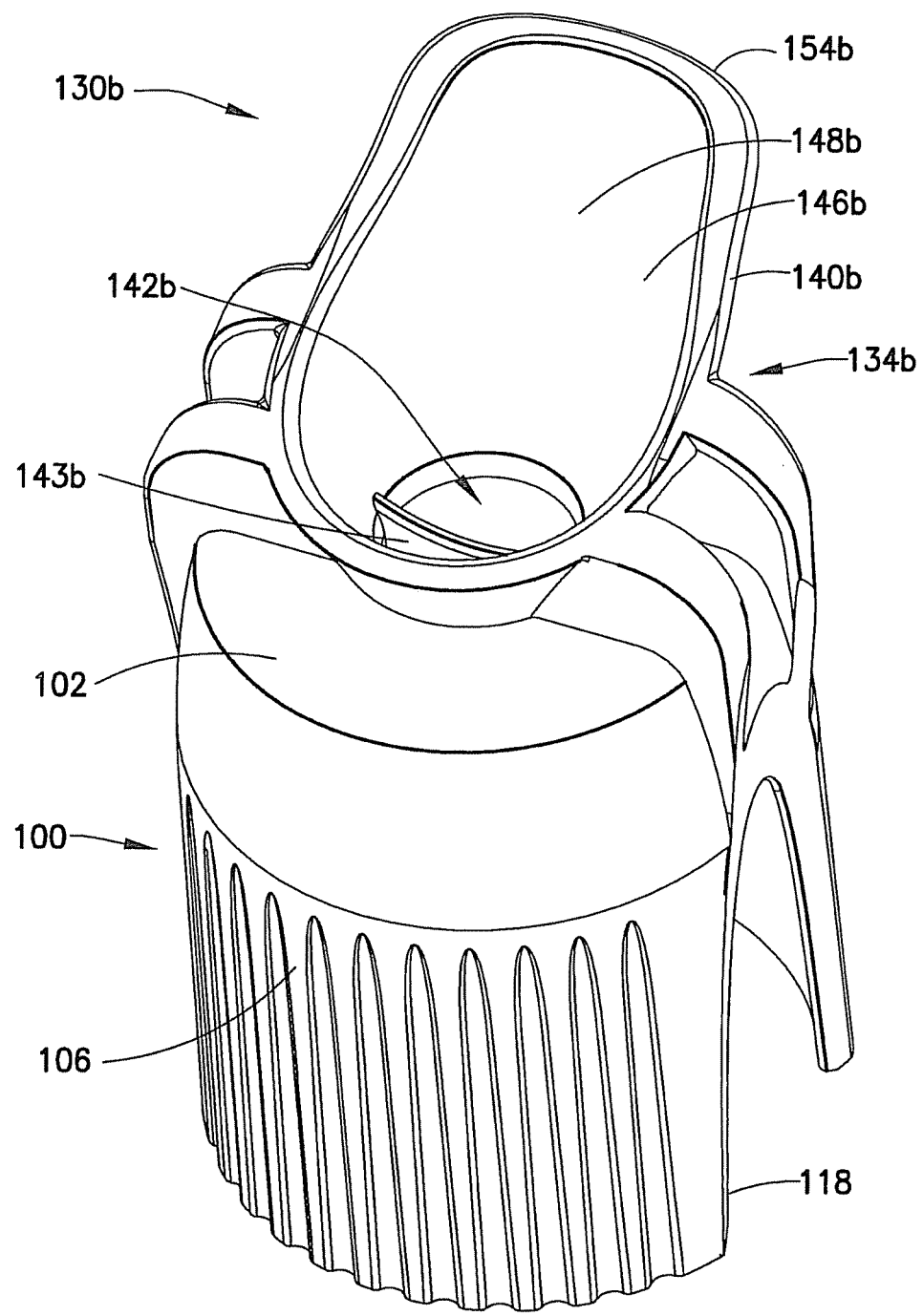
FIG. 25 is a front perspective view of a third embodiment of the collector optionally used with the collection device shown in FIG. 1.
Figure 26:
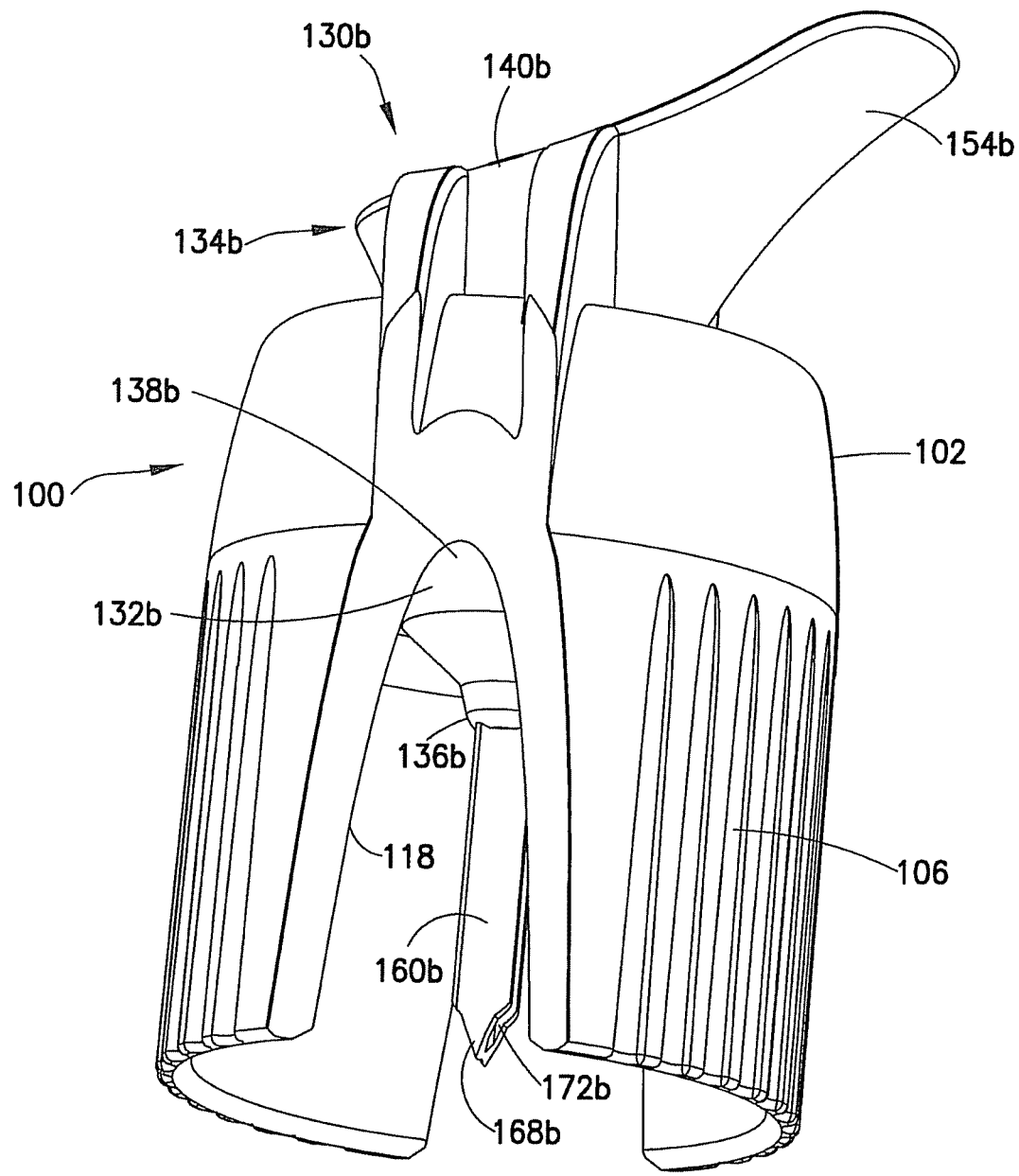
FIG. 26 is a side perspective view of the embodiment of the collector shown in FIG. 25.

Referring briefly to FIGS. 24-26, two additional embodiments of collector 130 are shown. In FIG. 24, collector 130a has the same features of collector 130 described in the foregoing, however, channel members 150a do not exhibit the "bulged" configuration of channel members 150 described previously. In this configuration, the channel members 150a do not extend above the level of rim portion 140a and rear wall 154a. In the embodiment of collector 130b depicted in FIGS. 25-26, channel members 150b are omitted entirely and reliance is made on capillary channels 152b now defined within central bore 142b in collector body 132b (and/or in rim 146b) to conduct a fluid sample flow under capillary action to capillary channel 172b in penetrating needle cannula 160b. Alternatively, channels 152b may be omitted and the interior of collector body 132b, including bore 142b and/or rim 146b, may be treated such that these surfaces are hydrophilic which will conduct fluid along these surfaces to needle cannula 160b. Such surface treatment may include an applied surfactant applied, for example, by plasma vapor deposition, to channel fluid downward to needle cannula 160b. All or portions of bore 142b and rim 146b may be treated. Additionally, collector 130b also illustrates that finger tabs 156b are optional in each embodiment described hereinabove and collector 130b may integrated as part of cap member 100 if desired. This configuration may be applied to each of collectors 130, 130a discussed previously.

Figure 22:
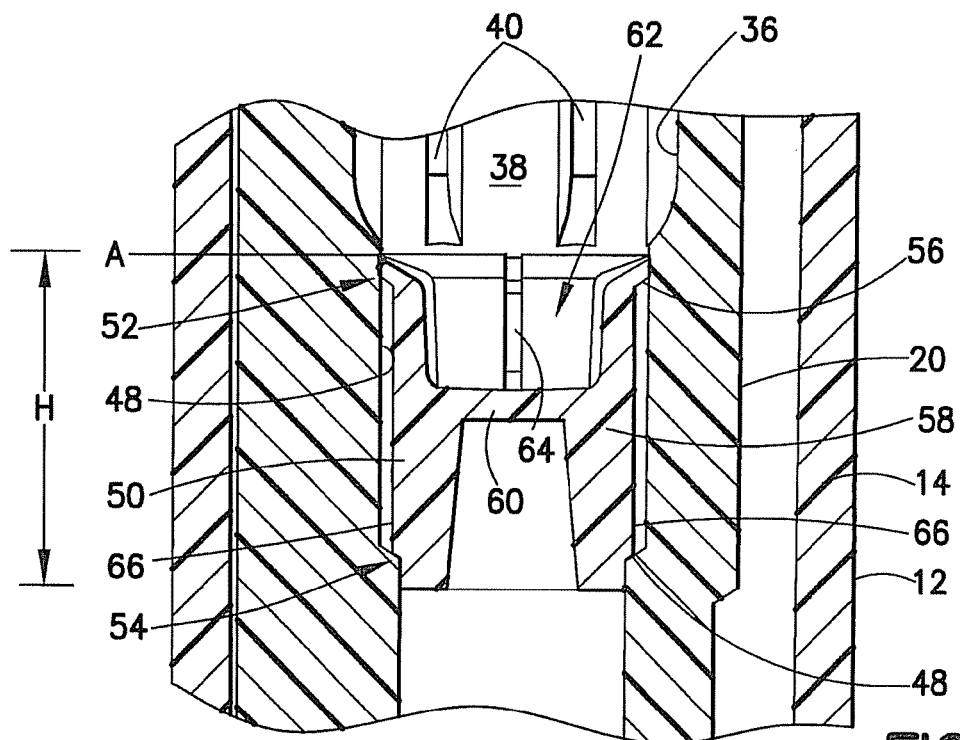
FIG. 22 is a detailed cross-sectional view showing the location of the wall element associated with the container assembly in a pre-centrifuge state of the container assembly.
Figure 23:
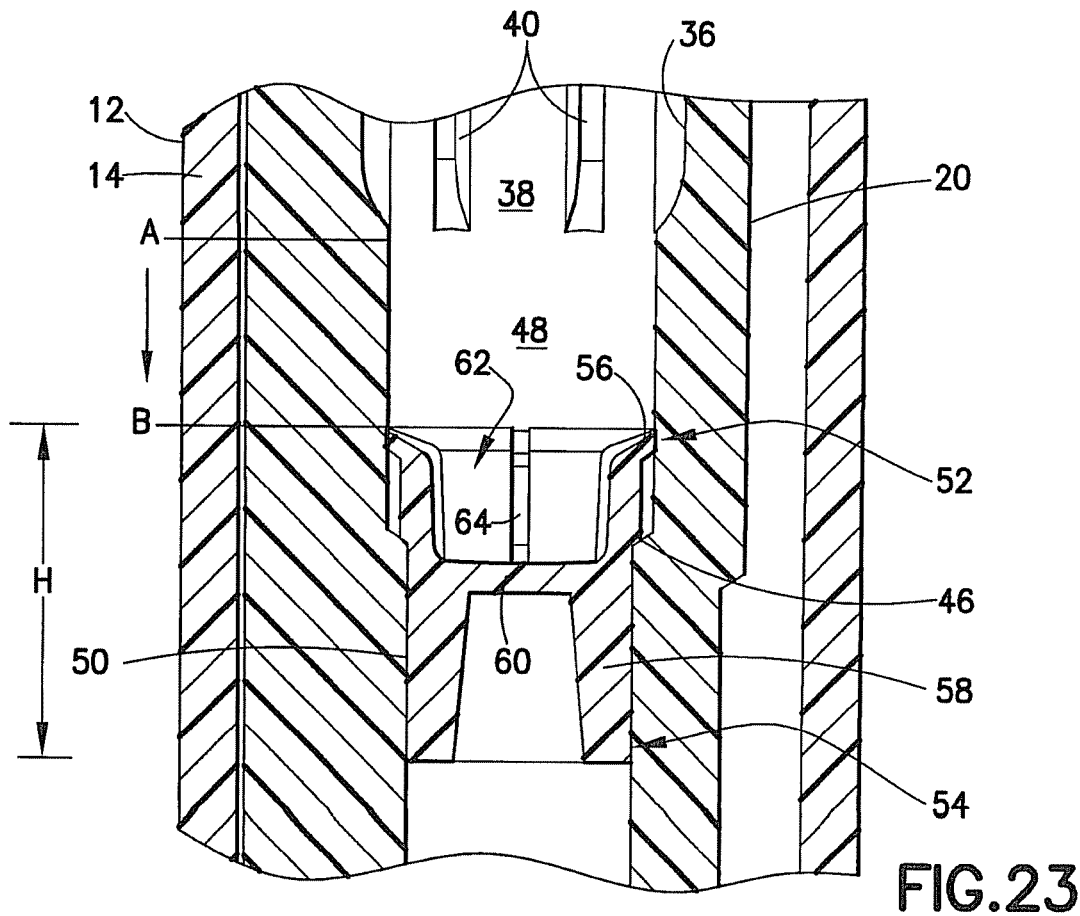
FIG. 23 is a detailed cross-sectional view showing the location of the wall element associated with the container assembly after centrifuging of the container assembly.

Referring now additionally to FIGS. 22-23, use of collection device 2 comprising container assembly 10 and collector 130 will now be described. In an assembled configuration, container assembly 10 and inner member 20 are disposed in outer container 12. As noted previously, in an initial "pre-centrifuge" state of container assembly 10, wall element 50 is disposed or situated in inner member 20 and located in the receiving space or area 48 associated with upper portion 42 of inner member 20. Moreover, in the assembled configuration, closure 70 and cap member 100 interface with inner member 20 and outer container 12 in the manner described previously. To use collection device 2, collector 130 is used to gain access to the fluid sample chamber 116 in container assembly 10. This is accomplished by a user piercing the closure body 72 of closure 70 with the penetrating needle cannula 160 associated with collector 130. Penetrating needle cannula 160 is inserted into proximal recess 98 in closure body 72 and pierces the container body 72 at this location. Once collector 130 is associated with container assembly 10, as best shown in FIG. 3, a fluid sample may be taken from a patient. Typically, a small puncture wound is made in the patient's fingertip by a lancet or similar device and the patient's fingertip is inserted into the rim portion 140 on collector body 132 of collector 130. The provision of "bulged" channel members 150 on collector body 132 guides the placement of the patient's fingertip within the collection area 148 of collector body 132. As the fluid sample, in this example blood, is extracted from the patient's fingertip, the small quantity of blood "drips" garnered as a result of a small puncture wound may not flow easily due to surface tension forces. In order to overcome these forces, the blood "drips" are channeled into capillary channels 152 defined by channel members 150. As noted previously, these capillary channels 152 connect with capillary channel 172 in penetrating needle cannula 160 which is separated from vent channel 170 by dividing wall 144 as described previously. Any blood "drips" that do not adequately enter capillary channels 152, for example, by missing the capillary channels 152 are channeled into capillary channels (not shown) in central bore 142 defined by the sidewall 138 of collector body 132, and these capillary channels likewise lead to the capillary channel 172. In view of the foregoing, it will be appreciated that interconnecting capillary channels 152, 172 provide a fluid path for small volume blood samples or "drips" to be directed into the fluid sample chamber 116 of container assembly 10. As noted previously, one of the channels 170, 172 in puncturing needle cannula 160 operates to channel the small volumes of blood into the fluid sample chamber 116 of container assembly 10 (i.e., capillary channel 172) while the second channel operates as a vent channel 170 to atmospheric pressure to enable the venting of air within the fluid sample chamber 116 to the atmosphere as blood fills the fluid sample chamber 116.

Once the blood volumes begin to enter fluid sample chamber 116 via puncturing needle cannula 160, the blood has a tendency due to surface tension to adhere to sidewall elements bounding or defining the fluid sample chamber 116. To channel blood to the bottom of fluid sample chamber 116, blood in capillary channel 172 typically migrates outward to enter capillary channels 84 in the distal recess 82 defined at the end of tapered portion 80 of closure body 72. Blood enters capillary channels 84 and is conducted by these capillary channels 84 outward to inner surface 38 of inner member 20. As noted previously, distal circumferential edge 85 of tapered portion or barrel 80 of closure body 72 provides a sufficient access route or edge for a capillary fluid sample to pass outward to the inner surface 38 of inner member 20 and enter capillary channels 40 therein. Capillary channels 40 conduct blood volume downward to wall element 50 and the capillary channels 64 therein conduct the blood volume into the cup-shaped recess or cavity 62 defined by wall element 50. As blood volume builds up above wall element 50, fluid sample chamber 116 is filled. A visual indication of when fluid sample chamber 116 is filled with fluid is provided by viewing the area around tapered portion 80 of closure body 72 of closure 70 through sidewall 14 of outer container 12. As noted previously, cutouts 118 are desirably provided in opposing sides of outer wall 106 of cap member 100 so that the visual-indication fill feature provided by interconnecting annular "flash" cavities 112, 114, described previously, is available for external inspection to a user of container assembly 10.

Once a fluid sample, such as blood, is present in fluid sample chamber 116, collector 130 may be removed from container assembly 10. It is often desirable to centrifuge the fluid sample, typically blood, to separate its constituent elements into layers as mentioned previously. Often, after centrifuging is complete, it is desirable to place the container assembly 10, now containing a separated fluid sample, in one or more diagnostic machines. However, it is also possible to place container assembly 10 directly into such diagnostic machines, such as hematology devices, without centrifuging when it is desired to test a whole, "un-separated" blood sample. In order for some diagnostic machines to operate properly, a small head space or volume may be necessary above the level of fluid in the container assembly 10. However, if container assembly 10 is filled substantially to the level of collar portion 86 of closure body 72 of closure 70, which will be indicated by the visual-indication fill feature provided by the interconnecting annular "flash" cavities 112, 114, described previously, some diagnostic machines may not work properly. Wall element 50 is used to optionally provide a small head space or volume during the centrifuging process as mentioned previously. However, this head space is not always necessary in diagnostic machines. In these situations, wall element 50 may be one of the embodiments described previously that does not exhibit a "wedging" movement during centrifuging. In these alternative embodiments, wall element 50 simply defines the lower boundary of fill chamber 116.

An initial, "pre-centrifuge" state of wall element 50 is shown in FIG. 22 wherein the wall element 50 is disposed or situated in inner member 20 and located in the receiving space or area 48 associated with upper portion 42 of inner member 20. The location or level of the upper end 52 of wall element 50 is denoted by the letter A in FIG. 22. When container assembly 10 is exposed to centrifugal force in a conventional centrifuge machine as an example, wall element 50 wedges downward by the methods and manner described previously (namely, radial compression of external flanges 66 and/or radial compression of all or portions of the body of wall element 50), whereby the upper end 52 of wall element 50 is now located further down in inner member 20 as denoted by the letter B in FIG. 23. In one embodiment, the wall element 50 has an element height H, and the distance the wall element 50 travels within the inner member 20 is less than element height H. In such a configuration, the element height H is less than the distance the wall element 50 travels between the first location A and the second location B. As wall element 50 moves downward in inner member 20 when container assembly 10 is exposed to centrifugal force in a conventional centrifuge machine, a small head space or volume is made available or defined above the fluid sample level in container assembly 10. It will be appreciated that while wall element 50 has specific application to container assembly 10 described in this disclosure, it may have general use in any fluid collection and centrifuging application where it is desired to provide a small head space volume above a fluid sample after centrifuging the fluid sample. Typically, the distance from level A to level B is about one-half to three-quarters of the height or length of the wall element 50.

While several embodiments of a collection device and container assembly adapted to collect a fluid sample under capillary action and associated methods were described in the foregoing detailed description, those skilled in the art may make modifications and alterations to these embodiments without departing from the scope and spirit of the invention. Accordingly, the foregoing description is intended to be illustrative rather than restrictive.

What is claimed is:

1. A container assembly comprising:
   an outer container comprising a closed bottom, an open top, and a sidewall extending between the closed bottom and the open top, the closed bottom, the open top, and the sidewall defining an interior of the outer container;
   a hollow inner member disposed within the interior of the outer container and having an inner surface defining at least one capillary channel, the inner member comprising a first end adjacent the open top of the outer container, a second end, and an outer sidewall extending between the first end and the second end, the outer sidewall seated against the sidewall of the outer container; and
   a closure having a proximal end and a distal end, the proximal end of the closure seated at least partially within the first end of the inner member and concurrently within the outer container to seal the inner member and the interior of the outer container and define a fluid sample chamber, the distal end of the closure defining a recessed area shaped to direct fluid under capillary action to the at least one capillary channel in the inner member.

2. A container assembly as claimed in claim 1, wherein the hollow member extends from the open top to the closed bottom of the outer container and comprises a second end supported against the closed bottom.

3. A container assembly as claimed in claim 1, wherein the at least one capillary channel extends longitudinally along the inner surface of the inner member.

4. A container assembly as claimed in claim 3, wherein the at least one capillary channel extends only a portion of a length of inner surface of the inner member.

5. A container assembly as claimed in claim 1, wherein the at least one capillary channel comprises a plurality of capillary channels equally distributed around the inner surface of the inner member.

6. A container assembly as claimed in claim 1, wherein the recessed area of the closure distal end is concave or conically-shaped and at least one capillary channel is defined in the recessed area.

7. A container assembly as claimed in claim 1, wherein the first end of the inner member defines a socket portion for receiving the proximal end of the closure, and the proximal end of the closure comprises a collar portion for sealing against the socket portion.

8. A container assembly as claimed in claim 7, wherein the socket portion comprises retaining tabs for retaining the collar portion in the socket portion.

9. A container assembly as claimed in claim 7, wherein the collar portion comprises at least two sealing shoulders contacting the socket portion.

10. A container assembly as claimed in claim 9, wherein the at least two sealing shoulders contact the socket at approximately orthogonal locations.

11. A container assembly as claimed in claim 1, wherein the closure comprises a closure body tapering inward from the closure proximal end to the closure distal end to define an annular space about the closure body with the inner surface of the inner member.

12. A container assembly as claimed in claim 1, further comprising a cap member in engagement with the closure.

* * * * *